US008221327B2

(12) United States Patent
Lee et al.

(10) Patent No.: US 8,221,327 B2
(45) Date of Patent: Jul. 17, 2012

(54) THERAPY CONTROL BASED ON CARDIOPULMONARY STATUS

(75) Inventors: Kent Lee, Shoreview, MN (US); Jeffrey E. Stahmann, Ramsey, MN (US); Jesse W. Hartley, White Bear Lake, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 12/688,274

(22) Filed: Jan. 15, 2010

(65) Prior Publication Data

US 2010/0174154 A1   Jul. 8, 2010

Related U.S. Application Data

(63) Continuation of application No. 10/930,346, filed on Aug. 31, 2004, now Pat. No. 7,662,101.

(60) Provisional application No. 60/504,477, filed on Sep. 18, 2003, provisional application No. 60/504,723, filed on Sep. 18, 2003.

(51) Int. Cl.
*A61B 5/08*   (2006.01)

(52) U.S. Cl. ........................................................ 600/529

(58) Field of Classification Search .................. 600/309, 600/529–543
See application file for complete search history.

(56) References Cited

U.S. PATENT DOCUMENTS

| | | |
|---|---|---|
| 4,312,734 A | 1/1982 | Nichols |
| 4,365,636 A | 12/1982 | Barker |
| 4,390,405 A | 6/1983 | Hahn et al. |
| 4,562,841 A | 1/1986 | Brockway et al. |
| 4,702,253 A | 10/1987 | Nappholz et al. |
| 4,721,110 A | 1/1988 | Lampadius |
| 4,777,962 A | 10/1988 | Watson et al. |
| 4,802,485 A | 2/1989 | Bowers et al. |
| 4,807,629 A | 2/1989 | Baudino et al. |
| 4,813,427 A | 3/1989 | Schlaefke et al. |
| 4,827,935 A | 5/1989 | Geddes et al. |
| 4,830,008 A | 5/1989 | Meer |

(Continued)

FOREIGN PATENT DOCUMENTS

EP   0750920   1/1997

(Continued)

OTHER PUBLICATIONS

Mansfield, D. et al., *Effects of Continuous Positive Airway Pressure on Lung Function in Patients with Chronic Obstructive Pulmonary Disease and Sleep Disordered Breathing*, Respirology 365-70 (1999). Abstract only.

(Continued)

*Primary Examiner* — Charles A Marmor, II
*Assistant Examiner* — Karen Toth
(74) *Attorney, Agent, or Firm* — Hollingsworth Davis, LLC

(57) ABSTRACT

Methods and systems provide an approach to therapy control based on assessment of a patient's cardiopulmonary status. Conditions sensed via sensors of an external respiratory therapy device are used to assess a patient's cardiopulmonary status. The respiratory therapy device sensors may be utilized alone or in combination with other sensors to determine cardiopulmonary status of a patient. Therapy delivered to the patient is controlled based on the cardiopulmonary status assessment. For example, therapy delivered to the patient may be initiated, terminated, and/or modified based on the assessed cardiopulmonary status of the patient. Cardiopulmonary status assessment, therapy control, or both, are performed by an implantable device.

18 Claims, 37 Drawing Sheets

U.S. PATENT DOCUMENTS

| | | |
|---|---|---|
| 4,836,219 A | 6/1989 | Hobson et al. |
| 4,856,524 A | 8/1989 | Baker, Jr. |
| 4,875,477 A | 10/1989 | Waschke et al. |
| 4,886,064 A | 12/1989 | Strandberg |
| 4,928,688 A | 5/1990 | Mower |
| 4,958,632 A | 9/1990 | Duggan |
| 4,961,423 A | 10/1990 | Canducci |
| 4,982,738 A | 1/1991 | Griebel |
| 5,024,222 A | 6/1991 | Thacker |
| 5,036,849 A | 8/1991 | Hauck et al. |
| 5,047,930 A | 9/1991 | Martens et al. |
| 5,105,354 A | 4/1992 | Nishimura |
| 5,123,425 A | 6/1992 | Shannon, Jr. et al. |
| 5,146,918 A | 9/1992 | Kallok et al. |
| 5,174,287 A | 12/1992 | Kallok et al. |
| 5,178,156 A | 1/1993 | Takishima et al. |
| 5,183,038 A | 2/1993 | Hoffman et al. |
| 5,187,657 A | 2/1993 | Forbes |
| 5,199,424 A | 4/1993 | Sullivan et al. |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,243,979 A | 9/1993 | Stein et al. |
| 5,245,995 A | 9/1993 | Sullivan et al. |
| 5,259,373 A | 11/1993 | Gruenke et al. |
| 5,275,159 A | 1/1994 | Griebel |
| 5,280,791 A | 1/1994 | Lavie |
| 5,284,136 A | 2/1994 | Hauck et al. |
| 5,299,118 A | 3/1994 | Martens et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,363,842 A | 11/1994 | Mishelevich et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | Kenknight et al. |
| 5,397,342 A | 3/1995 | Heil, Jr. et al. |
| 5,398,682 A | 3/1995 | Lynn |
| 5,404,877 A | 4/1995 | Nolan et al. |
| 5,411,031 A | 5/1995 | Yomtov |
| 5,466,245 A | 11/1995 | Spinelli et al. |
| 5,483,969 A | 1/1996 | Testerman et al. |
| 5,485,851 A | 1/1996 | Erickson |
| 5,487,755 A | 1/1996 | Snell et al. |
| 5,517,983 A | 5/1996 | Deighan et al. |
| 5,520,176 A | 5/1996 | Cohen |
| 5,522,382 A | 6/1996 | Sullivan et al. |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,590,648 A | 1/1997 | Mitchell et al. |
| 5,593,431 A | 1/1997 | Sheldon |
| 5,603,732 A | 2/1997 | Dahl et al. |
| 5,605,151 A | 2/1997 | Lynn |
| 5,632,281 A | 5/1997 | Rayburn |
| 5,645,570 A | 7/1997 | Corbucci |
| 5,693,000 A | 12/1997 | Crosby et al. |
| 5,697,951 A | 12/1997 | Harpstead et al. |
| 5,701,894 A | 12/1997 | Cherry et al. |
| 5,704,345 A | 1/1998 | Berthon-Jones |
| 5,713,933 A | 2/1998 | Condie et al. |
| 5,715,812 A | 2/1998 | Deighan et al. |
| 5,720,771 A | 2/1998 | Snell |
| 5,738,102 A | 4/1998 | Lemelson |
| 5,792,188 A | 8/1998 | Starkweather et al. |
| 5,794,615 A | 8/1998 | Estes |
| 5,800,470 A | 9/1998 | Stein et al. |
| 5,802,188 A | 9/1998 | McDonough |
| 5,814,087 A | 9/1998 | Renirie |
| 5,826,579 A | 10/1998 | Remmers et al. |
| 5,836,987 A | 11/1998 | Baumann et al. |
| 5,839,430 A | 11/1998 | Cama |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,902,250 A | 5/1999 | Verrier et al. |
| 5,911,218 A | 6/1999 | DiMarco |
| 5,916,243 A | 6/1999 | KenKnight et al. |
| 5,944,680 A | 8/1999 | Christopherson et al. |
| 5,957,861 A | 9/1999 | Combs et al. |
| 5,964,778 A | 10/1999 | Fugoso et al. |
| 5,970,975 A | 10/1999 | Estes et al. |
| 5,974,340 A | 10/1999 | Kadhiresan |
| 5,974,349 A | 10/1999 | Levine |
| 5,981,011 A | 11/1999 | Overcash et al. |
| 6,015,388 A | 1/2000 | Sackner et al. |
| 6,021,351 A | 2/2000 | Kadhiresan et al. |
| 6,026,320 A | 2/2000 | Carlson et al. |
| 6,044,297 A | 3/2000 | Sheldon et al. |
| 6,044,298 A | 3/2000 | Salo et al. |
| 6,045,513 A | 4/2000 | Stone et al. |
| 6,047,203 A | 4/2000 | Sackner et al. |
| 6,055,454 A | 4/2000 | Heemels |
| 6,059,725 A | 5/2000 | Steinschneider |
| 6,064,910 A | 5/2000 | Andersson et al. |
| 6,076,015 A | 6/2000 | Hartley et al. |
| 6,091,973 A | 7/2000 | Colla et al. |
| 6,091,986 A | 7/2000 | Keimel |
| 6,099,479 A | 8/2000 | Christopherson et al. |
| 6,105,575 A | 8/2000 | Estes et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,144,866 A | 11/2000 | Miesel et al. |
| 6,148,814 A | 11/2000 | Clemmer et al. |
| 6,155,976 A | 12/2000 | Sackner et al. |
| 6,161,042 A | 12/2000 | Hartley et al. |
| 6,165,155 A | 12/2000 | Jacobsen et al. |
| 6,168,568 B1 | 1/2001 | Gavriely |
| 6,181,961 B1 | 1/2001 | Prass |
| 6,190,326 B1 | 2/2001 | McKinnon et al. |
| 6,200,265 B1 | 3/2001 | Walsh et al. |
| 6,212,435 B1 | 4/2001 | Lattner et al. |
| 6,221,011 B1 | 4/2001 | Bardy |
| 6,236,873 B1 | 5/2001 | Holmström |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,261,238 B1 | 7/2001 | Gavriely |
| 6,263,244 B1 | 7/2001 | Mann et al. |
| 6,264,606 B1 | 7/2001 | Ekwall et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,286,508 B1 | 9/2001 | Remmers et al. |
| 6,287,264 B1 | 9/2001 | Hoffman |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Hartley et al. |
| 6,351,670 B1 | 2/2002 | Kroll |
| 6,353,759 B1 | 3/2002 | Hartley et al. |
| 6,357,444 B1 | 3/2002 | Parker |
| 6,358,203 B2 | 3/2002 | Bardy |
| 6,361,494 B1 | 3/2002 | Lindenthaler |
| 6,361,522 B1 | 3/2002 | Scheiner et al. |
| 6,363,270 B1 | 3/2002 | Colla et al. |
| 6,366,813 B1 | 4/2002 | DiLorenzo |
| 6,368,284 B1 | 4/2002 | Bardy |
| 6,368,287 B1 | 4/2002 | Hadas |

| Patent Number | Date | Inventor(s) |
|---|---|---|
| 6,371,922 B1 | 4/2002 | Baumann et al. |
| 6,375,621 B1 | 4/2002 | Sullivan |
| 6,375,623 B1 | 4/2002 | Gavriely |
| 6,387,907 B1 | 5/2002 | Hendricks et al. |
| 6,397,845 B1 | 6/2002 | Burton |
| 6,398,728 B1 | 6/2002 | Bardy |
| 6,398,739 B1 | 6/2002 | Sullivan et al. |
| 6,409,675 B1 | 6/2002 | Turcott |
| 6,409,676 B2 | 6/2002 | Ruton et al. |
| 6,411,848 B2 | 6/2002 | Kramer et al. |
| 6,411,850 B1 | 6/2002 | Kay et al. |
| 6,414,183 B1 | 7/2002 | Sakamoto et al. |
| 6,415,183 B1 | 7/2002 | Scheiner et al. |
| 6,424,865 B1 | 7/2002 | Ding |
| 6,431,171 B1 | 8/2002 | Burton |
| 6,438,407 B1 | 8/2002 | Ousdigian et al. |
| 6,438,410 B2 | 8/2002 | Hsu et al. |
| 6,440,066 B1 | 8/2002 | Bardy |
| 6,442,413 B1 | 8/2002 | Silver |
| 6,447,459 B1 | 9/2002 | Larom |
| 6,449,503 B1 | 9/2002 | Hsu |
| 6,454,719 B1 | 9/2002 | Greenhut |
| 6,459,929 B1 | 10/2002 | Hopper et al. |
| 6,463,326 B1 | 10/2002 | Hartley et al. |
| 6,467,333 B2 | 10/2002 | Lewis et al. |
| 6,468,219 B1 | 10/2002 | Njemanze |
| 6,480,733 B1 | 11/2002 | Turcott |
| 6,487,443 B2 | 11/2002 | Olson et al. |
| 6,497,658 B2 | 12/2002 | Roizen et al. |
| 6,527,729 B1 | 3/2003 | Turcott |
| 6,542,775 B2 | 4/2003 | Ding et al. |
| 6,547,743 B2 | 4/2003 | Brydon |
| 6,572,543 B1 | 6/2003 | Christopherson et al. |
| 6,574,507 B1 | 6/2003 | Bonnet |
| 6,580,944 B1 | 6/2003 | Katz et al. |
| 6,589,188 B1 | 7/2003 | Street et al. |
| 6,595,928 B2 | 7/2003 | Mansy et al. |
| 6,597,951 B2 | 7/2003 | Kramer et al. |
| 6,600,949 B1 | 7/2003 | Turcott |
| 6,606,993 B1 | 8/2003 | Wiesmann et al. |
| 6,641,542 B2 | 11/2003 | Cho et al. |
| 6,648,833 B2 | 11/2003 | Hampton et al. |
| 6,658,292 B2 | 12/2003 | Kroll et al. |
| 6,662,032 B1 | 12/2003 | Gavish et al. |
| 6,679,250 B2 | 1/2004 | Walker et al. |
| 6,694,186 B2 | 2/2004 | Bardy |
| 6,723,055 B2 | 4/2004 | Hoffman |
| 6,731,984 B2 | 5/2004 | Cho et al. |
| 6,741,885 B1 | 5/2004 | Park et al. |
| 6,748,252 B2 | 6/2004 | Lynn et al. |
| 6,752,765 B1 | 6/2004 | Jensen et al. |
| 6,752,766 B2 | 6/2004 | Kowallik et al. |
| 6,765,062 B2 | 7/2004 | Chin et al. |
| 6,770,022 B2 | 8/2004 | Mechlenburg et al. |
| 6,770,029 B2 | 8/2004 | Iliff |
| 6,773,404 B2 | 8/2004 | Poezevera et al. |
| 6,786,866 B2 | 9/2004 | Odagiri et al. |
| 6,810,287 B2 | 10/2004 | Zhu et al. |
| 6,830,548 B2 | 12/2004 | Bonnet et al. |
| 6,832,609 B2 | 12/2004 | Wright et al. |
| 6,881,192 B1 | 4/2005 | Park |
| 6,890,305 B2 | 5/2005 | Irie et al. |
| 6,895,275 B2 | 5/2005 | Markowitz et al. |
| 6,904,320 B2 | 6/2005 | Park et al. |
| 6,910,481 B2 | 6/2005 | Kimmel et al. |
| 6,912,419 B2 | 6/2005 | Hill et al. |
| 6,928,324 B2 | 8/2005 | Park et al. |
| 6,932,084 B2 | 8/2005 | Estes et al. |
| 6,951,539 B2 | 10/2005 | Bardy |
| 6,964,641 B2 | 11/2005 | Cho et al. |
| 6,988,498 B2 | 1/2006 | Berthon-Jones et al. |
| 6,999,817 B2 | 2/2006 | Park et al. |
| 7,025,730 B2 | 4/2006 | Cho et al. |
| 7,027,871 B2 | 4/2006 | Burnes et al. |
| 7,062,308 B1 | 6/2006 | Jackson |
| 7,065,409 B2 | 6/2006 | Mazar |
| 7,089,936 B2 | 8/2006 | Madaus et al. |
| 7,092,755 B2 | 8/2006 | Florio |
| 7,101,341 B2 | 9/2006 | Tsukashima et al. |
| 7,117,036 B2 | 10/2006 | Florio |
| 7,127,290 B2 | 10/2006 | Girouard |
| 7,127,300 B2 | 10/2006 | Mazar et al. |
| 7,130,687 B2 | 10/2006 | Cho et al. |
| 7,136,704 B2 | 11/2006 | Schulman |
| 7,155,278 B2 | 12/2006 | King et al. |
| 7,160,252 B2 | 1/2007 | Cho |
| 7,184,817 B2 | 2/2007 | Zhu et al. |
| 7,189,204 B2 | 3/2007 | Ni et al. |
| 7,204,805 B2 | 4/2007 | Dean |
| 7,206,635 B2 | 4/2007 | Cho et al. |
| 7,207,945 B2 | 4/2007 | Bardy |
| 7,212,862 B2 | 5/2007 | Park et al |
| 7,225,013 B2 | 5/2007 | Geva et al. |
| 7,225,021 B1 | 5/2007 | Park et al. |
| 7,225,809 B1 | 6/2007 | Bowen et al. |
| 7,231,250 B2 | 6/2007 | Band et al. |
| 7,245,971 B2 | 7/2007 | Park et al. |
| 7,252,640 B2 | 8/2007 | Ni et al. |
| 7,258,670 B2 | 8/2007 | Bardy |
| 7,269,459 B1 | 9/2007 | Koh |
| 7,277,757 B2 | 10/2007 | Casavant et al. |
| 7,302,295 B2 | 11/2007 | Stahmann et al. |
| 7,308,311 B2 | 12/2007 | Sorensen et al. |
| 7,314,046 B2 | 1/2008 | Schroeder et al. |
| 7,376,463 B2 | 5/2008 | Salo et al. |
| 7,396,333 B2 | 7/2008 | Stahmann et al. |
| 7,400,928 B2 | 7/2008 | Hatlestad |
| 7,413,549 B1 | 8/2008 | Koh |
| 7,425,200 B2 | 9/2008 | Brockway et al. |
| 7,428,468 B2 | 9/2008 | Takemura et al. |
| 7,435,221 B1 | 10/2008 | Bharmi et al. |
| 7,438,686 B2 | 10/2008 | Cho |
| 7,440,795 B2 | 10/2008 | Poezevara |
| 7,445,601 B2 | 11/2008 | Kline |
| 7,469,697 B2 | 12/2008 | Lee et al. |
| 7,575,553 B2 | 8/2009 | Stahmann et al. |
| 7,664,546 B2 | 2/2010 | Hartley et al. |
| 7,678,061 B2 | 3/2010 | Lee et al. |
| 2001/0018547 A1 | 8/2001 | Mechlenburg et al. |
| 2002/0103442 A1* | 8/2002 | Mulligan et al. .............. 600/513 |
| 2002/0120207 A1 | 8/2002 | Hoffman |
| 2002/0185130 A1 | 12/2002 | Wright et al. |
| 2002/0193685 A1 | 12/2002 | Mate et al. |
| 2003/0023184 A1 | 1/2003 | Pitts-Crick et al. |
| 2003/0050538 A1 | 3/2003 | Naghavi et al. |
| 2003/0055461 A1 | 3/2003 | Girouard et al. |
| 2003/0083241 A1 | 5/2003 | Young |
| 2003/0100925 A1 | 5/2003 | Pape et al. |
| 2003/0163059 A1 | 8/2003 | Poezevera et al. |
| 2003/0178031 A1 | 9/2003 | Du Pen et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0216789 A1 | 11/2003 | Deem et al. |
| 2004/0059240 A1 | 3/2004 | Cho et al. |
| 2004/0073093 A1 | 4/2004 | Hatlestad |
| 2004/0088027 A1 | 5/2004 | Burnes et al. |
| 2004/0122487 A1 | 6/2004 | Hatlestad et al. |
| 2004/0128161 A1 | 7/2004 | Mazar et al. |
| 2004/0133079 A1 | 7/2004 | Mazar et al. |
| 2004/0134496 A1 | 7/2004 | Cho et al. |
| 2004/0138719 A1* | 7/2004 | Cho et al. ........................ 607/42 |
| 2004/0163648 A1 | 8/2004 | Burton |
| 2004/0210151 A1 | 10/2004 | Tsukashima et al. |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0043652 A1 | 2/2005 | Lovett et al. |
| 2005/0043772 A1 | 2/2005 | Stahmann et al. |
| 2005/0065572 A1 | 3/2005 | Hartley et al. |
| 2005/0085865 A1 | 4/2005 | Tehrani |
| 2005/0101841 A9 | 5/2005 | Kaylor et al. |
| 2005/0107838 A1 | 5/2005 | Lovett et al. |
| 2005/0142070 A1 | 6/2005 | Hartley et al. |
| 2005/0159784 A1 | 7/2005 | Arceta |
| 2006/0195041 A1 | 8/2006 | Lynn et al. |
| 2006/0293714 A1 | 12/2006 | Salo et al. |
| 2007/0055115 A1 | 3/2007 | Kwok et al. |

| | | | |
|---|---|---|---|
| 2007/0083241 | A1* | 4/2007 | Bardy ............................. 607/3 |
| 2007/0112388 | A1 | 5/2007 | Salo |
| 2007/0149860 | A1* | 6/2007 | Lynn et al. ..................... 600/300 |
| 2007/0150014 | A1 | 6/2007 | Kramer et al. |
| 2007/0161873 | A1 | 7/2007 | Ni et al. |
| 2007/0282215 | A1 | 12/2007 | Ni et al. |
| 2008/0045813 | A1 | 2/2008 | Phuah et al. |
| 2009/0007918 | A1 | 1/2009 | Darkin et al. |

FOREIGN PATENT DOCUMENTS

| | | |
|---|---|---|
| EP | 0770407 | 5/1997 |
| EP | 0940155 A | 8/1999 |
| EP | 0940155 | 9/1999 |
| EP | 1151718 | 11/2001 |
| EP | 1162125 | 12/2001 |
| EP | 1172125 | 1/2002 |
| EP | 1317943 | 6/2003 |
| WO | WO8402080 | 6/1984 |
| WO | WO9203983 | 3/1992 |
| WO | WO99/04841 | 2/1999 |
| WO | WO00/01438 | 1/2000 |
| WO | WO0001438 | 1/2000 |
| WO | WO 00/17615 | 3/2000 |
| WO | WO0017615 | 3/2000 |
| WO | WO 0240096 | 5/2002 |
| WO | WO02/087696 | 7/2002 |
| WO | WO03075744 | 9/2003 |
| WO | WO2004/062485 | 7/2004 |
| WO | WO2005028029 | 3/2005 |
| WO | WO2005053788 | 6/2005 |

OTHER PUBLICATIONS

Reddel et al., *Analysis of Adherence to Peak Flow Monitoring When Recording of Data is Electronic*, BMJ 146-147 (2002).

U.S. Office Action dated Dec. 10, 2008 for U.S. Appl. No. 10/930,346, 13 pages.

U.S. Office Action dated Aug. 3, 2009 for U.S. Appl. No. 10/930,346, 19 pages.

Ajilore et al., Nightcap: Laboratory and home-based evaluation of a portable sleep monitor, 32 Psychophysiology, 32-98, 1995. Abstract only.

Altshule et al., The Effect of Position on Periodic Breathing in Chronic Cardiac Decomposition, New Eng. Journal of Med., vol. 259, No. 22, pp. 1064-1066, Nov. 27, 1958.

Balaban et al., Feasibility of Screening for Sleep Apnea Using Pacemaker Impedance Sensor, NASPE, 2001.

Bradley et al, Cardiac Output Response to Continuous Positive Airway Pressure In Congestive Heart Failure, 145 Am. Rev. Respir. Dis. 377-382, 1992. Abstract only.

Bradley et al., Pathophysiologic and Therapeutic Implications of Sleep Apnea in Congestive Heart Failure, 3 J. Cardiac Failure 223-240, 1996. Abstract only.

Bradley et al., Sleep Apnea and Heart Failure, Part I: Obstructive Sleep Apnea, 107 Circulation 1671-1678, 2003.

Buda et al., Effect Of Intrathoracic Pressure On Left Ventricular Performance, 301 Engl. J. Med. 453-459, 1979. Abstract only.

Calvin et al., Positive End-Expiratory Pressure (PEEP) Does Not Depress Left Ventricular Function in Patients With Pulmonary Edema, 124 Am. Rev. Respir. Dis. 121-128 (1981). (Abstract only)

Junyu et al., Posture Detection Algorithm Using Multi Axis DC-Accelerometer, Pace vol. 22. Apr. 1999. Abstract only.

Dark et al., Breathing Pattern Abnormalities and Arterial Oxygen Desaturation During Sleep in the Congestive Heart Failure Syndrome, Chest, 6:833-6, Jun. 1987.

De Hoyos et al., Haemodynamic Effects of Continuous Positive Airway Pressure in Humans With Normal and Impaired Left Ventricular Function, 88 Clin. Sci. (Lond). 173-8, 1995. Abstract only.

Garrigue et al., Benefit of Atrial Pacing in Sleep Apnea Syndrome, 346 N. Engl. J. Med. 404-412, 2002. Abstract only.

Garrigue et al., Night Atrial Overdrive with DDD Pacing: A New Therapy for Sleep Apnea Syndrome, NASPE 21st Annual Scientific Sessions, Apr. 2000, vol. 23, No. 4, Part II, #591, 1 page, Abstract Only.

Garrigue et al., Night Atrial Overdrive with DDD Pacing Results in a Significant Reduction of Sleep Apnea Episodes and QOL Improvement in Heart Failure Patients, NASPE, 2001.

Giardino et al., Respiratory Sinus Arrhythmia is Associated with the Efficiency of Pulmonary Gas Exchange in Healthy Humans, 284 Am. J. Physiol. H1585-1591, 2003.

Hanson et al., Cardiac Gated Ventilation, 2433 SPIE 303-308, 1995.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769, 1999.

Hoffman et al., Cheyne-Stokes Respiration in Patients Recovering from Acute Cardiogenic Pulmonary Edema, Chest, 97:410-12, 1990.

Javaheri et al., Sleep Apnea in 81 Ambulatory Male Patients with Stable Heart Failure: Types and Their Prevalences, Consequences, and Presentations, 97 Circulation 2154-2159, 1998.

Kaye et al., Acute Effects of Continuous Positive Airway Pressure on Cardiac Sympathetic Tone in Congestive Heart Failure, 103 Circulation 2336-2338, 2001.

Laude et al., Effects of Breathing Pattern on Blood Pressure and Heart Rate Oscillations in Humans, 20 Clin. Exp. Pharmol. Phisiol 619, 625, 1993. Abstract only.

Lenique et al., Ventilatory and Hemodynamic Effects of Continuous Positive Airway Pressure in Left Heart Failure, 155 Am. J. Respir. Crit. Care Med. 500-505, 1997. Abstract only.

Mehta et al., Effects of Continuous Positive Airway Pressure on Cardiac Volumes In Patients With Ischemic and Dilated Cardiomyopathy, 161 Am. J. Respir. Crit. Care Med. 128-134, 2000.

Naughton et al., Effects of Continuous Positive Airway Pressure on Intrathoracic and Left Ventricular Transmural Pressure in Congestive Heart Failure, 91 Circulation 1725-1731, 1995.

Pinsky et al., Hemodynamic Effect of Cardiac Cycle-Specific Increases in Intrathoracic Pressure, 6 J. Appl. Physiol. 604-612, 1986.

Potkin et al., Effect of positive end-expiratory pressure on right and left ventricular function in patients with the adult respiratory distress syndrome, 135 Am. Rev. Respir. Dis. 307-311, 1987. Abstract only.

Rees et al., Paroxysmal Nocturnal Dyspnoea and Periodic Respiration, The Lancet, Dec. 22-29, pp. 1315-1317, 1979. Abstract only.

Roche et al., Screening of Obstructive Sleep Apnea Syndrome by Heart Rate Variability Analysis, 100 Circulation 1411-1455, 1999.

Scharf, Effects of Continuous Positive Airway Pressure on Cardiac Output in Experimental Heart Failure, 19 Sleep S240-2, 1996. Abstract only.

Steltner et al., Diagnosis of Sleep Apnea by Automatic Analysis of Nasal Pressure and Forced Oscillation Impedance. Am. Journal Respiratory Critical Care Medicine, vol. 165, pp. 940-944, 2002.

Tkacova et al., Left Ventricular Volume in Patients with Heart Failure and Cheyne-Strokes Respiration during Sleep, Am. Journal, Respir. Crit. Care Med., vol. 156, pp. 1549-1555, 1997.

Vanninen et al., Cardiac Sympathovagal Balance During Sleep Apnea Episodes, 16 Clin. Physiol. 209-216, 1996. Abstract only.

Verrier et al., Sleep, dreams, and sudden death: the case for sleep as an autonomic stress test for the heart, 31 Cardiovascular Research 181-211, 1996.

Verrier et al., Sleep Related Cardiovascular Risk: New Home-Based Monitoring Technology for Improved Diagnosis and Therapy, 2 A.N. E. 158-175, 1997.

Waldemark et al., Detection of Apnea using Short Window FFT Technique and Artificial Neural Network, 3390 SPIE International Society for Optical Engineering 122-133, 1998.

Weber et al. Effect of CPAP and BIPAP on stroke volume in patients with obstructive sleep apnea syndrome. Pneumolgie; 49(3):233-5, 1995. Abstract only.

Young et al., The Occurrence of Sleep-Disordered Breathing Among Middle Aged Adults, N. Engl. J. Med. 1230-1235, 1993. Abstract only.

Office Action from U.S. Appl. No. 10/930,508 dated Jun. 25, 2007, 15 pages.

Office Action Response submitted Nov. 21, 2007 to office action dated Jun. 25, 2007 from U.S. Appl. No. 10/930,508, 12 pages.

Office Action from U.S. Appl. No. 10/930,508 dated Feb. 14, 2008, 13 pages.

Office Action Response submitted Apr. 14, 2008 to office action dated Feb. 14, 2008 from U.S. Appl. No. 10/930,508, 12 pages.
Office Action from patent U.S. Appl. No. 10/930,508 dated Jul. 9, 2008, 14 pages.
Office Action Response submitted Nov. 6, 2008 to office action dated Jul. 9, 2008 from U.S. Appl. No. 10/930,508, 9 pages.
Notice of Allowance dated Feb. 24, 2009 from U.S. Appl. No. 10/943,508, 21 pages.
Office Action from U.S. Appl. No. 10/943,077 dated Nov. 26, 2008, 21 pages.
Office Action Response submitted Mar. 19, 2009 to office action dated Nov. 26, 2008 from U.S. Appl. No. 10/943,077, 11 pages.
Office Action from U.S Appl. No. 10/943,077 dated Jul. 7, 2009, 16 pages.
Office Action Response submitted Oct. 7, 2009 to office action dated Jul. 7, 2009 from U.S. Appl. No. 10/943,077, 11 pages.
Office Action from U.S. Appl. No. 10/943,077 dated Jan. 21, 2010, 15 pages.
Office Action Response submitted Mar. 11, 2010 to office action dated Jan. 21, 2010 from U.S. Appl. No. 10/943,077, 12 pages.
Notice of Allowance dated Sep. 21, 2009 from U.S. Appl. No. 10/930,346, 8 pages.
Office Action Response dated Aug. 24, 2009 from U.S. Appl. No. 10/930,346, 10 pages.
Office Action Response dated May 7, 2009 from U.S. Appl. No. 10/930,346, 9 pages.
Examiner Interview Summary dated Apr. 17, 2009 from U.S. Appl. No. 10/930,346, 2 pages.
Office Action dated Apr. 1, 2010 from U.S. Appl. No. 10/943,077, 3 pages.
Notice of Allowance dated Feb. 24, 2009 from U.S. Appl. No. 10/930,508, 8 pages.
Examiner Interview Summary dated Oct. 14, 2008 from U.S. Appl. No. 10/930,508, 4 pages.
International Search Report dated Dec. 22, 2004 from PCT Application No. PCT/US2004/030787, 8 pages.
Office Action dated May 9, 2007 from European Application No. 04784602.7, 3 pages.
Office Action dated Jan. 10, 2008 from European Application No. 04784602.7, 3 pages.
Office Action Response dated Apr. 17, 2008 from European Application No. 04784602.7, 10 pages.
Office Action dated Dec. 21, 2008 from European Application No. 04784602.7, 6 pages.
International Search Report and Written Opinion from European Application No. 08075738.8 dated Jul. 26, 2010, 4 pages.

* cited by examiner

DETECTION OF PULMONARY DISEASES/DISORDERS
Conditions and Sensors

Fig. 6B-2

| Sensor Group | Right Ventricular Egram | Left Ventricular Egram | RA Egram | LA Egram | Accelerometer |
|---|---|---|---|---|---|
| CRM Sensors | X | X | X | X | X |
| CPAP Sensors |  |  |  |  |  |
| External Non-CPAP/CRM | X | X | X | X | X |

Physiological Changes vs. Sensor Measurements

Sensor columns (left to right):
- RV R-wave Temporal Location
- RV R-wave Morphology
- RV R-wave Amplitude
- RV T-wave Temporal Location
- RV T-wave Morphology
- RV QT Segment Elevation
- LV R-wave Temporal Location
- LV R-wave Morphology
- LV R-wave Amplitude
- LV T-wave Temporal Location
- LV T-wave Morphology
- LV QT Segment Elevation
- RA P-wave Temporal Location
- RA P-wave Morphology
- RA P-wave Amplitude
- RA P-wave Temporal Location
- RA P-wave Morphology
- RA P-wave Amplitude
- Activity
- Heart Sounds
- Respiration Sounds
- Posture Physiological Changes (rows):
- Pulmonary Function
- Low FEV, FVC, FEV/FVC
- Low FEF
- High FRC, TLC
- High RV
- High Lung Compliance
- Slow Exhalation
- Tachypnea
- Shallow (Low Tidal Volume) Breathing
- High Minute Ventilation
- Respiratory Failure
- Reduced Diffusion Capacity DETECTION OF PULMONARY DISEASES/DISORDERS
Conditions and Sensors

| | Vent Gas | | Vent Flow | | Vent Pres | | pH | Finger | | Scale | Temp | Data Base | | Direct Patient Query | | | | |
|---|---|---|---|---|---|---|---|---|---|---|---|---|---|---|---|---|---|---|
| Sensor group | | | | | | | | | | | | | | | | | | |
| CRM Sensors | | | | | | | x | | | | | | | | | | | |
| CPAP Sensors | x | | x | | | | | | | | | | | | | | | |
| External Non-CPAP/CRM | x | | x | | x | | | x | | x | x | x | | x | | | | |
| | Exhaled %O2 | Exhaled %CO2 | Inspiratory Flow | Expiratory Flow | Inspiratory Pressure | Expiratory Pressure | Blood pH | Relative Pulse Pressure | Blood pO2 | Weight | Core Temperature | Medications | History | Pain | Abnormal Breathing/Coughing | Duration of Symptoms | Falls | Other Symptoms |
| Physiological Changes | | | | | | | | | | | | | | | | | | |
| Dyspnea | | | | | | | | | | | | | | | | | | |
| Non-specific Dyspnea | X | X | X | X | | | | | | | | | | | D | D | | |
| Orthopnea | X | X | X | X | | | | | | | | | | | D | D | | |
| Exertional Dyspnea | X | X | X | X | | | | | | | | | | | D | D | | |
| Paroxysmal Nocturnal Dyspnea | X | X | X | X | | | | | | | | | | | D | D | | |
| Blood / Respiratory Gases | | | | | | | | | | | | | | | | | | |
| Cyanosis | X | | | | | | | | X | | | | | | | | | |
| Hypoxemia | X | | | | | | | | X | | | | | | | D | | |
| Hypercapnia | | X | | | | | X | | | | | | | | | | | |
| Low pCO2 | | X | | | | | X | | | | | | | | | | | |
| Arterial acidosis | | | | | | | X | | | | | | | | | | | |
| High Alveolar-Arterial pO2 Diff | X | | | | | | | | X | | | | | | | | | |
| Respiratory Sounds | | | | | | | | | | | | | | | | | | |
| Wheezing | | | | | | | | | | | | | | | | | X | X |
| Crackles | | | | | | | | | | | | | | | | | X | X |
| Rhonchi | | | | | | | | | | | | | | | | | | |
| Fiction Rub | | | | | | | | | | | | | | | | | | |
| Attenuated Breath Sounds | | | | | | | | | | | | | | | | | | |
| Snoring | | | | | | | | | | | | | | | | D | | D |

Fig. 6C-1

DETECTION OF PULMONARY DISEASES/DISORDERS
Conditions and Sensors

| | RV R-wave Temporal Location | RV R-wave Morphology | RV R-wave Amplitude | RV T-wave Temporal Location | RV T-wave Morphology | RV QT Segment Elevation | LV R-wave Temporal Location | LV R-wave Morphology | LV R-wave Amplitude | LV T-wave Temporal Location | LV T-wave Morphology | LV QT Segment Elevation | RA P-wave Temporal Location | RA P-wave Morphology | RA P-wave Amplitude | RA P-wave Temporal Location | RA P-wave Morphology | Activity | Heart Sounds | Respiration Sounds | Posture |
|---|---|---|---|---|---|---|---|---|---|---|---|---|---|---|---|---|---|---|---|---|---|
| Right Ventricular Egram | | | | | | | | | | | | | | | | | | | | | |
| Left Ventricular Egram | | | | | | | | | | | | | | | | | | | | | |
| RA Egram | | | | | | | | | | | | | | | | | | | | | |
| LA Egram | | | | | | | | | | | | | | | | | | | | | |
| Accelerometer | | | | | | | | | | | | | | | | | | | | | |

Physiological Changes

| Other Pulmonary | | | | | | | | | | | | | | | | | | | | | |
|---|---|---|---|---|---|---|---|---|---|---|---|---|---|---|---|---|---|---|---|---|---|
| Hemoptysis | | | | | | | | | | | | | | | | | | | | | |
| Cough | | | | | | | | | | | | | | | | | | | | | X |
| Pleuritic Chest Pain | | | | | | X | | | | | X | | | | | | | | | | X |
| Local Inflammation | | | | | | | | | | | | | | | | | | | | | |
| Excess Mucous Production | | | | | | | | | | | | | | | | | | | | | X |
| Chest Pain | | | | | | X | | | | | X | | | | | | | | | | |
| Respiratory Infection (sight. elev. WBC) | | | | | | | | | | | | | X | X | | | | | | | |
| Pulmonary Mucus | | | | | | | | | | | | | | | | | | | | | |
| Overinflat. Lungs→barrel-shaped chest | | | | | | | | | | | | | | | | | | | | | |
| Alveolar wall breakdown | | | | | | | | | | | | | | | | | | | | | |
| Mucosal Pulmonary Edema | | | | | | | | | | | | | | | | | | | | | |
| Ventilation-perfusion mismatch | | | | | | | | | | | | | | | | | | | | | |
| Subepithelial Fibrosis (chronically) | | | | | | | | | | | | | | | | | | | | | |
| Respiratory Muscle Fatigue | | | | | | | | | | | | | | | | | | | | | X |
| High small airway resistance | | | | | | | | | | | | | | | | | | | | | |
| Hoarseness | | | | | | | | | | | | | | | | | | | | | |

| | CRM Sensors | CPAP Sensors | External Non-CPAP/CRM |
|---|---|---|---|
| Right Ventricular Egram | X | X | |
| Left Ventricular Egram | X | X | |
| RA Egram | X | X | |
| LA Egram | X | X | |
| Accelerometer | X | | X |

Fig. 6D-1

DETECTION OF PULMONARY DISEASES/DISORDERS
Conditions and Sensors

| | Transthoracic Impedance | | | | | | | Blood Pressure | | | | | Blood Gas | |
|---|---|---|---|---|---|---|---|---|---|---|---|---|---|---|
| | Respiration Rate | Tidal Volume | Minute Ventilation | Inspiration Time | Exhalation Time | Heart Motion Morphology | DC Thoracic Impedance | Systolic Blood Pressure | Diastolic Blood Pressure | Pulse Pressure | Wedge Pressure | Contractility (dP/dt) | Blood pO2 / pCO2 | Arterial / Venous pO2 |
| CRM Sensors | x | | | | | | | x | | | | | x | |
| CPAP Sensors | | | | | | | | | | | | | | |
| External Non-CPAP/CRM | x | | | | | | | x | | | | | x | |

Physiological Changes

| Other Pulmonary | Respiration Rate | Tidal Volume | Minute Ventilation | Inspiration Time | Exhalation Time | Heart Motion Morphology | DC Thoracic Impedance | Systolic BP | Diastolic BP | Pulse Pressure | Wedge Pressure | Contractility | Blood pCO2 | Arterial/Venous pO2 |
|---|---|---|---|---|---|---|---|---|---|---|---|---|---|---|
| Hemoptysis | | | | | | | | | | | | | | |
| Cough | | | x | | | | | | | | | | | |
| Pleuritic Chest Pain | | | x | x | x | | | | | | | | | |
| Local Inflammation | | | | | | | | | | | | | | |
| Excess Mucous Production | | | | x | x | | | | | | | | | |
| Chest Pain | | x | x | x | x | | | | | | | | | |
| Respiratory Infection (slight. elev. WBC) | | | x | x | x | | | | x | | | | | |
| Pulmonary Mucus | | | | x | x | | | | | | | | | |
| Overinflat Lungs→barrel-shaped chest | | | x | x | x | | | | x | | | | | |
| Alveolar wall breakdown | | | | | | | | | | | | | | |
| Mucosal Pulmonary Edema | | x | x | x | x | | | | | | | | | |
| Ventilation-perfusion mismatch | | | | | | | | | | | | | x | |
| Subepithelial Fibrosis (chronically) | | | | | | | | | | | | | | |
| Respiratory Muscle Fatigue | | | x | x | x | | | | | | | | | x |
| High small airway resistance | | | x | x | x | | | | | | | | | x |
| Hoarseness | | | | | | | | | | | | | | |

DETECTION OF PULMONARY DISEASES/DISORDERS

| Physiological Changes | COPD - Obstructive | | | Restrictive | | | Infectious | | | Pul Vasculature | | | Pleural | | Rhythm | | Other |
|---|---|---|---|---|---|---|---|---|---|---|---|---|---|---|---|---|---|
| | Chronic Bronchitis | Emphysema | Asthma | Sarcoidosis | Pulmonary Fibrosis | Pneumoconiosis | Bronchitis | Pneumonia | Bronchiolitis | Tuberculosis | Bronchiectasis | Pulmonary Hypertension | Pulmonary Edema | Atelectasis | Pleural Effusion | Pneumothorax | Hemothorax (See Pleural Effusion) | Apnea (obstructive & central) | Hypopnea (obstructive & central) | Cheyne-Stokes Periodic Breathing | Lung Cancer | ARDS |
| Dyspnea | | | | | | | | | | | | | | | | | | | | | | |
| Non-specific Dyspnea | X | X | X | X | | | | X | X | X | X | X | X | X | X | | | | | | | |
| Orthopnea | X | X | | | | | | | | | | | X | | | | | | | | | |
| Exertional Dyspnea | X | | X | | X | | | | | | | X | | | | | | | | | | |
| Paroxysmal Nocturnal Dyspnea | | X | | | | | | | | | | | X | | | | | | | | | |
| Blood / Respiratory Gases | | | | | | | | | | | | | | | | | | | | | | |
| Cyanosis | X | X | X | | X | | | | X | | | | X | | | X | X | X | | | | |
| Hypoxemia | X | X | X | | X | | | X | X | | X | X | X | | | X | X | X | | | | |
| Hypercapnea | X | | X | | X | | | X | | | | | | | | X | X | X | | | | |
| Low pCO2 | | | | | X | | | | | | | | | | | X | X | X | | | | |
| Arterial acidosis | X | | | | | | | | | | | | | | | | | | | | | |
| High Alveolar-Arterial pO2 Diff | X | X | | | | | | | | | | | | X | | | | | | | | |
| Respiratory Sounds | | | | | | | | | | | | | | | | | | | | | | |
| Wheezing | X | | X | | | | | | X | | X | | | | | | | | | | | |
| Crackles | X | X | | | X | X | | X | | | X | | | | | | | | | | | |
| Rhonchi | X | | X | | | | | X | | | X | | | | | | | | | | | |
| Fiction Rub | | | | | | | | | | | | | | | | | | | | | | |
| Attenuated Breath Sounds | X | X | | | | | | | | | | | | | X | X | X | | | | | |
| Snoring | | | | | | | | | | | | | | | | | | | X | X | | | |

Fig. 6F-2

DETECTION OF PULMONARY DISEASES/DISORDERS

Pulmonary Diseases/Disorders (620-2)

Physiological Changes (604)

| Disease/Disorder | Category | Low FEV, FVC, FEV/FVC | Low FEF | High FRC, TLC | High RV | High Lung Compliance | Slow Exhalation | Tachypnea | Shallow (Low Tidal Volume) Breathing | High Minute Ventilation | Respiratory Failure | Reduced Diffusion Capacity |
|---|---|---|---|---|---|---|---|---|---|---|---|---|
| Chronic Bronchitis | Obstructive (COPD) | X | X |  | X |  | X | X |  |  |  | X |
| Emphysema | Obstructive (COPD) | X | X | X | X | X | X |  |  |  |  |  |
| Asthma | Obstructive |  |  |  |  |  |  |  |  |  |  |  |
| Sarcoidosis | Restrictive |  |  |  |  |  |  | X | X |  |  | X |
| Pulmonary Fibrosis | Restrictive |  |  |  |  |  |  | X | X |  |  |  |
| Pneumoconiosis | Restrictive |  |  |  |  |  |  | X | X |  |  |  |
| Bronchiolitis | Restrictive |  |  |  |  |  |  |  |  |  |  |  |
| Pneumonia | Infectious |  |  |  |  |  |  | X | X |  |  |  |
| Tuberculosis | Infectious |  |  |  |  |  |  |  |  |  |  |  |
| Bronchiectasis | Infectious |  |  |  |  |  |  |  |  |  |  |  |
| Pulmonary Hypertension | Pul Vasculature |  |  |  |  |  |  |  |  |  |  |  |
| Pulmonary Edema | Pul Vasculature |  |  |  |  |  |  | X |  |  |  |  |
| Atelectasis | Pul Vasculature |  |  |  |  |  |  | X |  |  |  |  |
| Pleural Effusion | Pleural |  |  |  |  |  |  | X |  |  |  |  |
| Hemothorax | Pleural |  |  |  |  |  |  |  |  |  | X |  |
| Pneumothorax | Pleural |  |  |  |  |  |  |  |  |  |  |  |
| Apnea (obstructive & central) | Rhythm |  |  |  |  |  |  |  |  |  |  |  |
| Hypopnea (obstructive & central) | Rhythm |  |  |  |  |  |  |  |  |  |  |  |
| Cheyne-Stokes | Rhythm |  |  |  |  |  |  |  |  |  |  |  |
| Periodic Breathing | Rhythm |  |  |  |  |  |  |  |  |  |  |  |
| Lung Cancer | Other |  |  |  |  |  |  |  |  |  |  |  |
| ARDS | Other |  |  |  |  |  |  | X |  |  |  |  |

DETECTION OF PULMONARY DISEASES/DISORDERS

Fig. 6G-1

| Physiological Changes / Other Pulmonary | COPD - Obstructive | | | Restrictive | | | | Infectious | | | | | Pul Vasculature | | | Pleural | | | Rhythm | | | Other | |
|---|---|---|---|---|---|---|---|---|---|---|---|---|---|---|---|---|---|---|---|---|---|---|---|
| | Chronic Bronchitis | Emphysema | Asthma | Sarcoidosis | Pulmonary Fibrosis | Pneumoconiosis | Bronchitis | Pneumonia | Bronchiolitis | Tuberculosis | Bronchiectasis | Pulmonary Hypertension | Pulmonary Edema | Atelectasis | Pulmonary Embolism | Pleural Effusion | Pneumothorax | Hemothorax (See Pleural Effusion) | Apnea (obstructive & central) | Hypopnea (obstructive & central) | Cheyne-Stokes Periodic Breathing | Lung Cancer | ARDS |
| Hemoptysis | X | X | | | | | X | X | | X | X | | | | | | | | | | | | |
| Cough | X | X | X | | X | X | X | X | X | X | X | | | | | | | | | | | | |
| Pleuritic Chest Pain | | | | | | | | X | | | | | | | | | | | | | | | |
| Local Inflammation | | | | | | | | X | X | | | | | | | | | | | | | | |
| Excess Mucous Production | X | | | | | | X | | | | | | | | | | | | | | | | |
| Chest Pain | X | | | | | | X | X | | X | | | | X | X | | | | | | | | |
| Respiratory Infection (slight. elev. WBC) | X | X | | | | | X | X | | | X | | | | | | | | | | | | |
| Pulmonary Mucus | X | X | | | | | | | | | X | | | | | | | | | | | | |
| Overinflat. Lungs→barrel-shaped chest | | X | | | | | | | | | | | | | | | | | | | | | |
| Alveolar wall breakdown | | X | | | | | | | | | | | | | | | | | | | | | |
| Mucosal Pulmonary Edema | | | X | | | | | | | | | | | | | | | | | | | | |
| Ventilation-perfusion mismatch | | | X | | | | | | | | | | | | | | | | | | | | |
| Subepithelial Fibrosis (chronically) | | | X | | | | | | | | | | | | | | | | | | | | |
| Respiratory Muscle Fatigue | | | | | | | | | | | | | | | | | | | | | | | |
| High small airway resistance | X | | | | | | | | | | | | | | | | | | | | | | |
| Hoarseness | | | | | | | | | | | X | | | | | | | | | | | | |

Fig. 6G-2

DETECTION OF PULMONARY DISEASES/DISORDERS

| Physiological Changes | Chronic Bronchitis | Emphysema | Asthma | Sarcoidosis | Pulmonary Fibrosis | Pneumoconiosis | Bronchitis | Pneumonia | Bronchiolitis | Tuberculosis | Bronchiectasis | Pulmonary Hypertension | Pulmonary Edema | Atelectasis | Pleural Effusion | Pneumothorax | Hemothorax | Apnea (obstructive & central) | Hypopnea (obstructive & central) | Cheyne-Stokes Periodic Breathing | Lung Cancer | ARDS |
|---|---|---|---|---|---|---|---|---|---|---|---|---|---|---|---|---|---|---|---|---|---|---|
| Cardiovascular | | | | | | | | | | | | | | | | | | | | | | |
| Pulmonary Hypertension | X | X | | X | X | | | | | X | X | | | | | | | | | | | |
| High Pulmonary Vascular Resistance | X | X | | | | | | | | X | | | | | | | | | | | | |
| Tachycardia | X | | | | | X | | | | | | | | | | | | | | | | |
| Circulatory Collapse | | | | | | | | | | | | | | X | | | | | | | | |
| Pulsus Paradoxicus | X | | | | | | | | | | | | | | | | | | | | | |
| Syncope | | | | | | | | | | | | | | | | | | | | | | |
| Hypertension | | | X | X | | | X | X | | | X | X | | | | | | | | | | |
| S3 Heart Sound | | | | | | | | X | | | | X | | | | | | | | | | |
| Split S2 Heart Sound | | | | | | | | | | | | | | | | | X | X | | | | |
| RV Hypertrophy | | | | | | | | | | | | | | | | X | X | X | | | | |
| Systolic Murmur | | | | | | | | | | | | | | | | | | | | | | |
| General Systemic | | | | | | | | | | | | | | | | | | | | | | |
| Fever | | | | | | | X | X | X | | X | | | | | | | | | | X | |
| Weight Loss | | | | | | | | | | X | | | | | | | | | | | | |
| Weight Gain | | | | | | | | | | | | | | | | | | | | | | |
| Night Sweats | | | | | | | | | | X | | | | | | | | | | | | |
| Peripheral Edema | | | | | | | | | | | | | | | | | | | | | | |
| High Hemoglobin | X | X | | X | | | | | | | X | | | | | X | X | | | | | |
| Fatigue | X | X | | X | | | | | | | X | | | | | X | X | | | | | |
| Joint Pain | | | X | | | | | | | | | | | | | | | X | | | | |
| Hypersomnolence | | | | | | | | | | | | | | | | | | | | | | X |

DETECTION OF CARDIAC DISEASES/DISORDERS
Conditions and Sensors

| Physiological Changes | LA Egram | | | Accelerometer | | | | Transthoracic Impedance | | | | | | |
|---|---|---|---|---|---|---|---|---|---|---|---|---|---|---|
| | LA P-wave Temporal Location | LA P-wave Morphology | LA P-wave Amplitude | Body Motion | Heart Sounds | Respiration Sounds | Posture | Respiration Rate | Tidal Volume | Minute Ventilation | Inspiration Time | Exhalation Time | Heart Motion Morphology | DC Thoracic Impedance |
| Pulmonary | | | | | | | | | | | | | | |
| Pulmonary Edema | | | | | | | | | | X | X | X | X | X |
| Pleural Effusion | | | | | | | | | | X | X | X | X | X |
| Tidal Volume | | | | | | | | | D | D | | | | |
| Cough at Rest | | | | | | X | | | | | | | | |
| Dyspnea | | | | | | X | | | X | X | X | X | X | |
| Respiration Rate | | | | | | | | X | | | | | | |
| Wheezing | | | | | | X | | | | | | | X | |
| General systemic | | | | | | | | | | | | | | |
| Central Apnea | X | | | | | | | X | | | | | | |
| Activity Level | X | | | X | | | | | | X | X | X | | |
| O₂ Saturation | | | | | | | | | X | X | | | | |
| Automonic Balance | X | | | | | | | | | | | | | |
| Heart Rate Variability (HRV) | X | | | | | | | | X | X | | | | |
| Heart Rate / Activity Profile | X | | | | | | | | X | X | | | | |
| Chenye-Stokes Respiration | X | | | | | | | | | | | | | |
| Weight | | | | | | | | | | | | | | X |

Fig. 6K-2

DETECTION OF CARDIAC DISEASES/DISORDERS

| Diseases/Disorders | | Physiological Changes (604) — Cardiac | | | | | | | | | | | |
|---|---|---|---|---|---|---|---|---|---|---|---|---|---|
| Category | Condition | Heart Rate | Blood Pressure | Pulse Pressure | Ectopic Beat (PVC) Density | ST Segment Elevation | Mitral Regurgitation | Hypertrophy | Chest Pain | Stoke Volume | Ventricular Contractility | Pulse Alternans | Syncope |
| Other | | X | | | | | | | | | | | |
| Hypertension | | X | | | | | | | | | | | |
| Heart Failure | Diastolic | X | | | | | | | | | | | |
| Heart Failure | Systolic | X | X | X | | | | | | | X | | |
| CAD | Low Output | X | | | | | | | | | | | |
| CAD | Congestion | X | | | | | | | | | | | |
| CAD | Ischemia | X | X | X | | | X | X | | X | X | X | X |
| CAD | Acute MI | X | X | X | X | X | X | | X | | | | |
| Rhythm | Chronic Atrial Tachy/Fib | X | X | X | X | X | X | | X | | | | X |
| Rhythm | Paroxymal Atrial Tachy/Fib | X | X | X | X | X | | | | | | | X |
| Rhythm | Ventricular Tachy/Fib | X | X | X | X | X | | | | X | X | | X |
| Rhythm | Bradycardia | X | | | X | | | | | | | | X |

DETECTION OF CARDIAC DISEASES/DISORDERS

| Physiological Changes | Rhythm | | | | Acute MI | Ischemia | CAD | | Heart Failure | | Hypertension | Other |
|---|---|---|---|---|---|---|---|---|---|---|---|---|
| | Bradycardia | Ventricular Tachy/Fib | Paroxysmal Atrial Tachy/Fib | Chronic Atrial Tachy/Fib | | | Low Output | Congestion | Systolic | Diastolic | | |
| Pulmonary | | | | | | | | | | | | |
| Pulmonary Edema | | | X | | | | X | | | | | |
| Pleural Effusion | | | | | | | X | | | | | |
| Tidal Volume | | X | | | X | | X | | | | | |
| Cough at Rest | | | X | | X | | X | | | | | |
| Dyspnea | | X | X | | X | | X | | | | | |
| Respiration Rate | | | | | | | X | | | | | |
| Wheezing | | | | | | | | | | | | |
| General systemic | | | | | | | | | | | | |
| Central Apnea | | | | | | | X | | | | | |
| Activity Level | X | X | X | | X | | X | | | | | |
| O₂ Saturation | X | X | | | X | | X | | | | | |
| Automonic Balance | | X | X | | X | | X | | | | | |
| Heart Rate Variability (HRV) | | X | X | | X | | X | | | | | |
| Heart Rate / Activity Profile | X | | X | | | | X | | | | | |
| Chenye-Stokes Respiration | | | | | | | X | | | | | |
| Weight | | | | | | | X | | | | | |

Fig. 6N

THERAPY CONTROL BASED ON CARDIOPULMONARY STATUS

RELATED PATENT DOCUMENTS

This application is a continuation of U.S. patent application Ser. No. 10/930,346, filed on Aug. 31, 2004, now U.S. Pat. No. 7,662,101, which claims the benefit of Provisional Patent Application Ser. No. 60/504,477 and 60/504,723, both filed on Sep. 18, 2003, to which Applicant claims priority under 35 U.S.C. §120 and 35 U.S.C. §119(e), respectively, and which are incorporated herein by reference in their entireties.

FIELD OF THE INVENTION

The present invention relates generally to controlling therapy based on the cardiopulmonary status of a patient.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. Diseases and disorders of the cardiac and pulmonary systems, are among the leading causes of acute and chronic illness in the world. For example, heart failure (HF) is a clinical syndrome that impacts a number of physiological processes, including respiration. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others. Other cardiac disorders include cardiac rhythm disorders, such as bradycardia (a heart rhythm that is too slow) and tachyarrhythmia (a heart rhythm that is too fast).

Pulmonary diseases or disorders may be organized into various categories, including, for example, breathing rhythm disorders, obstructive diseases, restrictive diseases, infectious diseases, pulmonary vasculature disorders, pleural cavity disorders, and others. Symptoms of pulmonary dysfunction may include symptoms such as apnea, dyspnea, changes in blood or respiratory gases, symptomatic respiratory sounds, e.g., coughing, wheezing, and general degradation of pulmonary function, among other symptoms.

Breathing rhythm disorders involve patterns of interrupted and/or disrupted breathing. Sleep apnea syndrome (SAS) and Cheyne-Stokes respiration (CSR) are examples of breathing rhythm disorders. Breathing rhythm disorders may be caused by an obstructed airway or by derangement of the signals from the brain controlling respiration. Sleep disordered breathing is particularly prevalent and is associated with excessive daytime sleepiness, systemic hypertension, increased risk of stroke, angina, and myocardial infarction. Breathing rhythm disorders can be particularly serious for patients concurrently suffering from cardiovascular deficiencies.

Obstructive pulmonary diseases may be associated with a decrease in the total volume of exhaled air flow caused by a narrowing or blockage of the airways. Examples of obstructive pulmonary diseases include asthma, emphysema and bronchitis. Chronic obstructive pulmonary disease (COPD) refers to chronic lung diseases that result in blocked air flow in the lungs. Chronic obstructive pulmonary disease generally develops over many years, typically from exposure to cigarette smoke, pollution, or other irritants. Over time, the elasticity of the lung tissue is lost, the lung's air sacs may collapse, the lungs may become distended, partially clogged with mucus, and lose the ability to expand and contract normally. As the disease progresses, breathing becomes labored, and the patient grows progressively weaker. Many people with COPD concurrently have both emphysema and chronic bronchitis.

Restrictive pulmonary diseases involve a decrease in the total volume of air that the lungs are able to hold. Often the decrease in total lung volume is due to a decrease in the elasticity of the lungs themselves, or may be caused by a limitation in the expansion of the chest wall during inhalation. Restrictive pulmonary disease may be the result of scarring from pneumonia, tuberculosis, or sarcoidosis. A decrease in lung volume may be caused by various neurological and muscular diseases affecting the neural signals and/or muscular strength of the chest wall and lungs. Examples of neurological and/or muscular diseases that may affect lung volume include poliomyelitis and multiple sclerosis. Lung volume deficiencies may also be related to congenital or acquired deformities of the chest.

Pulmonary dysfunctions may also involve disorders of the pleural cavity and/or pulmonary vasculature. Pulmonary vasculature disorders may include pulmonary hypertension, pulmonary edema, and pulmonary embolism. Disorders of the pleural cavity include conditions such as pleural effusion, pneumothorax, and hemothorax, for example.

Pulmonary diseases may be caused by infectious agents such as viral and/or bacterial agents. Examples of infectious pulmonary diseases include pneumonia, tuberculosis, and bronchiectasis. Other non-infectious pulmonary diseases include lung cancer and adult respiratory distress syndrome (ARDS), for example.

Therapy may be more effectively delivered to a patient to alleviate the diseases and disorders discussed above if the patient's cardiopulmonary status is known. Methods and systems for controlling therapy based on cardiopulmonary status are desirable.

SUMMARY OF THE INVENTION

Various embodiments of present invention involve methods and systems for controlling therapy based on the cardiopulmonary status of the patient. One embodiment of the invention involves a method for controlling a therapy delivered to a patient based on cardiopulmonary status. One or more physiological conditions are sensed using an external respiratory therapy device. The patient's cardiopulmonary status is assessed based on the sensed physiological conditions. Therapy delivered to the patient is controlled based on the patient's cardiopulmonary status. At least one of assessing the patient's cardiopulmonary status and controlling the therapy is performed at least in part implantably.

According to various aspects of the invention, the physiological conditions are sensed using the sensors of a disordered breathing therapy device. The sensed physiological conditions may include, for example, sensing respiratory pressure, flow, and/or exhaled gas concentration.

In accordance with another aspect of the invention, the sensor system of an additional medical device, different from the respiratory therapy device may be used to sense additional physiological conditions used to assess cardiopulmonary status. In one implementation, the additional medical device comprises an implantable cardiac therapy device.

In accordance with another embodiment of the invention, a medical therapy control system controls therapy based on a patient's cardiopulmonary status. The control system includes an external respiratory device including a sensor system configured to sense one or more physiological conditions. A cardiopulmonary status processor is coupled to the sensor system. The cardiopulmonary status processor is configured to determine a cardiopulmonary status of a patient based on the sensed physiological conditions. A therapy controller is configured to control a therapy delivered to the patient based on the patient's cardiopulmonary status. At least one of the cardiopulmonary status processor and the therapy controller include an implantable component.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
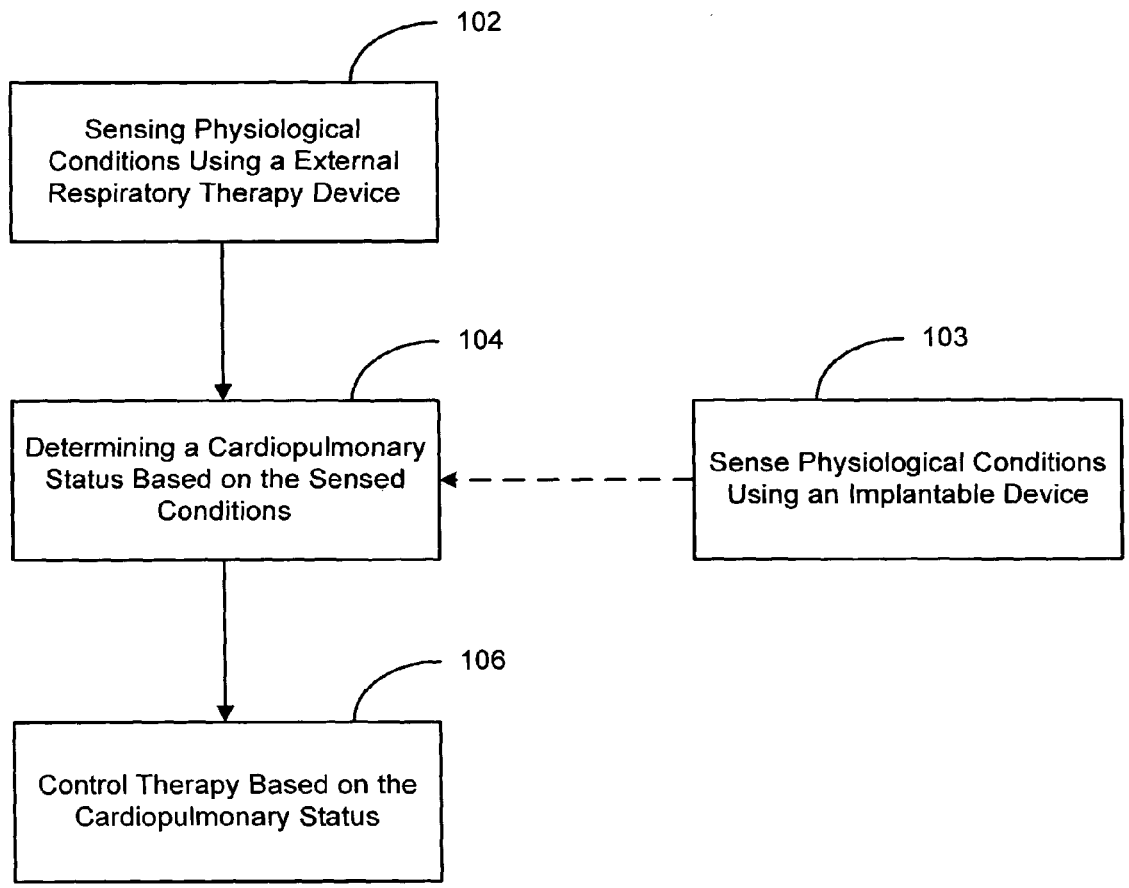
FIG. 1A is a flowchart illustrating a method of determining a presence of a non-rhythm pulmonary disease and delivering therapy in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

Pulmonary disorders may be organized into broad categories encompassing disorders related to breathing rhythm and non-rhythm related pulmonary diseases and/or disorders. Breathing rhythm disorders include various syndromes characterized by patterns of disordered breathing that produce insufficient respiration, for example, sleep apnea, hypopnea, and Cheyne-Stokes Respiration (CSR), among others. Breathing rhythm disorders are not necessarily accompanied by alteration of pulmonary structures.

Non-rhythm pulmonary diseases or disorders typically involve physical changes to lung structures, such as loss of elasticity of the lung tissue, obstruction of airways with mucus, limitation of the expansion of the chest wall during inhalation, fibrous tissue within the lung, excessive pressure in the pulmonary arteries, and/or other characteristics. Pulmonary diseases or disorders that are not rhythm-related are referred to herein as non-rhythm pulmonary diseases. Non-rhythm related pulmonary diseases/disorders may include obstructive pulmonary diseases, restrictive pulmonary diseases, infectious and non-infectious pulmonary diseases, pulmonary vasculature disorders, and pleural cavity disorders, for example.

Embodiments of the invention involve methods of controlling a therapy delivered to the patient, as illustrated in the flowchart of FIG. 1A. One or more physiological conditions are sensed 102 using the sensing system of an external respiratory therapy device. In various implementations, the external respiratory therapy device may comprise, for example, a gas therapy device, nebulizer, ventilator, positive airway pressure device, or other type of respiration therapy device. The patient's cardiopulmonary status is assessed 104 based on the sensed physiological conditions. Therapy delivered to the patient is controlled 106 based on the patient's cardiopulmonary status. The therapy may be used to treat breathing rhythm disorders, non-rhythm related pulmonary diseases/disorders, cardiac disorders, and/or other diseases or disorders affecting the patient.

In one embodiment, an implantable device may be used to sense 103 additional physiological conditions. The patient's cardiopulmonary status is assessed 104 based on the physiological conditions sensed by the external respiratory device and the additional physiological conditions sensed by the implantable device. At least one of assessing the patient's cardiopulmonary status and controlling the therapy is performed at least in part implantably. Implantably performing an operation comprises performing the operation using a component, device, or system that is partially or fully implanted within the body.

In one implementation, the presence of a cardiac and/or pulmonary disease or disorder is detected and therapy to treat the disease or disorder is delivered to the patient. The therapy may be modified to improve therapy effectiveness based on the assessment of the cardiac and/or pulmonary disease or disorder. In another embodiment of the invention, the patient's cardiopulmonary status is assessed and the therapy delivered to the patient is modified to enhance patient comfort or to achieve another result.

For example, the patient's cardiopulmonary status may be assessed based on sensed physiological conditions indicative of symptoms or physiological changes associated with a particular disease or disorder. A respiratory therapy device used to sense the physiological conditions may comprise, for example, a gas therapy device, nebulizer, ventilator, positive airway pressure device, or other type of respiration therapy device. In a preferred embodiment, the respiratory therapy device comprises a positive airway pressure device. Continuous positive airway pressure (CPAP) devices are frequently used to treat sleep apnea and/or other breathing rhythm disorders. A CPAP device may be used regularly during a patient's sleep time to prevent or treat sleep disordered breathing events. Use of a CPAP device for treatment of breathing rhythm disorders facilitates detection of rhythm-related and non-rhythm related pulmonary diseases. The CPAP device provides sensors available on a periodic basis, e.g., nightly, that may be used to sense conditions indicative of cardiopulmonary status.

In another implementation, assessment of the cardiopulmonary status of the patient is based on one or more physiological conditions sensed using a patient-external respiratory therapy device and on one or more additional physiological conditions sensed using a cardiac device. The cardiac device may comprise, for example, an implantable cardiac therapy device, such as a pacemaker, defibrillator, cardioverter, cardiac monitor, and/or cardiac resynchronizer.

In yet another implementation, assessment of the cardiopulmonary status of the patient is based on one or more physiological conditions sensed using a patient-external respiratory therapy device and one or more additional conditions sensed or detected using an additional patient-external device. The patient-external device may comprise, for example, a patient operated input device, a patient information database, or a network-connected server, for example.

According to one aspect of the invention, pulmonary function testing may be employed to detect physiological changes associated with the presence of cardiac and/or pulmonary disease. Pulmonary function tests may be used to evaluate lung mechanics, gas exchange, pulmonary blood flow, and blood gases and pH. They are used to evaluate patients in the diagnosis of pulmonary disease, assessment of disease development, or evaluation of the risk of pulmonary complications from surgery.

Pulmonary function testing is conventionally performed in a clinical setting and measures values indicative of the ability of the lungs to exchange oxygen and carbon dioxide. The total lung capacity (TLC) is divided into four volumes. The tidal volume ($V_T$) is the volume inhaled or exhaled in normal quiet breathing. The inspiratory reserve volume (IRV) is the maximum volume that can be inhaled following a normal quiet inhalation. The expiratory reserve volume (ERV) is the maximum volume that can be exhaled following a normal quiet exhalation. The residual volume (RV) is the volume remaining in the lungs following a maximal exhalation. The vital capacity (VC) is the maximum volume that can be exhaled following a maximal inhalation; $VC=IRV+V_T+ERV$. The inspiratory capacity (IC) is the maximum volume that can be inhaled following a normal quiet exhalation; $IC=IRV+V_T$. The functional residual capacity (FRC) is the volume remaining in the lungs following a normal quiet exhalation; $FRC=ERV+RV$.

The vital capacity and its components ($V_T$, IRV, ERV, IC) are typically measured using a spirometer, which is a device that measures the volumes of air inhaled and exhaled. The FRC is usually measured by the helium dilution method using a closed spirometry system. A known amount of helium is introduced into the system at the end of a normal quiet exhalation. When the helium equilibrates throughout the volume of the system, which is equal to the FRC plus the volume of the spirometer and tubing, the FRC is determined from the helium concentration. This test may underestimate the FRC of patients with emphysema. The FRC can be determined quickly and more accurately by body plethysmography. The residual volume and total lung capacity are determined from the FRC.

In the forced vital capacity (FVC) maneuver, the patient exhales as forcefully and rapidly as possible, beginning at maximal exhalation. Several parameters are determined from the spirogram. The FVC is the total volume of air exhaled during the maneuver; it is normally equal to the vital capacity. The forced expiratory volume (FEV) is the volume expired during a specified time period from the beginning of the test. The times used are 0.5, 1, 2, and 3 seconds; corresponding parameters are $FEW_{0.5}$, $FEV_{1.0}$, $FEV_{2.0}$, and $FEV_{3.0}$. The maximal expiratory flow rate (MEFR) is the slope of the line connecting the points where 200 ml and 1200 ml have been exhaled; it is also called $FEF_{200-1200}$ (forced expiratory flow). The maximal midexpiratory flow rate (MMFR, MMF) is the slope of the line connecting the points where 25 percent and 75 percent of the FVC have been exhaled; it is also called $FEF_{25-75\%}$.

The Maximal Voluntary Ventilation (MVV) is the maximal volume of air that can be breathed by the patient, expressed in liters per minute; it was formerly called maximal breathing capacity (MBC). The patient breathes as rapidly and deeply as possible for 12 to 15 seconds and the volume exhaled is determined by spirometry.

Various parameters related to pulmonary performance, some of which may be measured using sensors of a respiratory therapy device include, for example, tidal volume, minute ventilation, inspiratory reserve volume, forced expiratory volume, residual volume, and forced vital capacity, among other parameters. According to one embodiment, testing of some pulmonary function parameters may be performed using the ventilation pressure and ventilation flow sensors of a CPAP device or other patient-external respiratory therapy device. The pulmonary function testing may be used, for example, to assess a presence of restrictive and/or obstructive pulmonary disorders as indicated in FIGS. 1B-1D.

Pulmonary performance may be evaluated based on data acquired by the respiratory therapy device during normal and forced inspiration and expiration. From such data, pulmonary parameters including tidal volume, minute ventilation, forced expiratory volume, forced vital capacity, among other parameters may be determined.

Because the results of pulmonary function tests vary with size and age, the normal values are calculated using prediction equations or nomograms, which give the normal value for a specific age, height, and sex. The prediction equations are derived using linear regression on the data from a population of normal subjects. The observed values are usually reported as a percentage of the predicted value. Abnormal test results may show either an obstructive or restrictive pattern. Sometimes, both patterns are present.

Figure 1B:
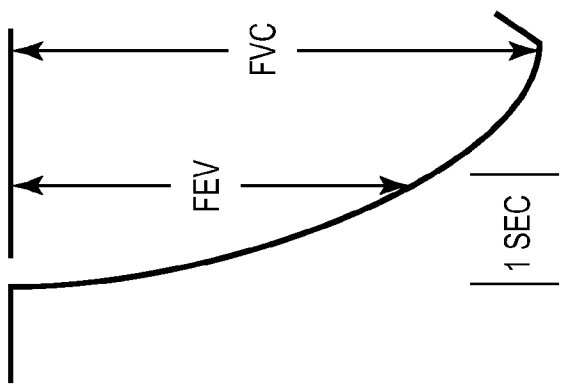
FIGS. 1B-1D are graphs of normal, obstructive and restrictive respiratory patterns, respectively, in accordance with embodiments of the invention.
Figure 1C:
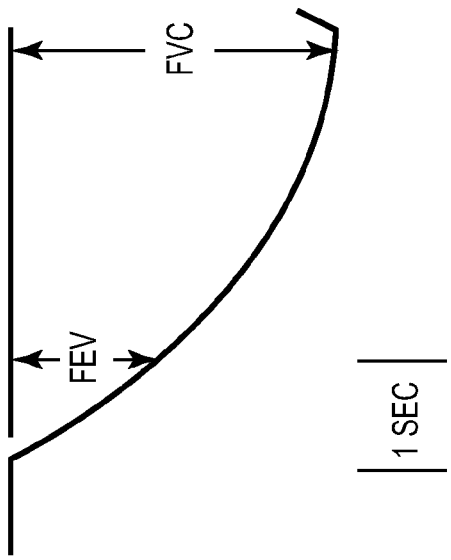
Figure 1D:
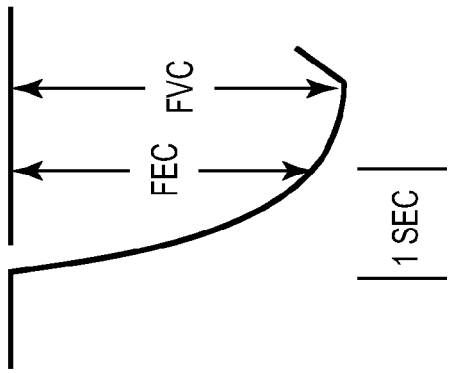

FIG. 1B illustrates a normal respiratory pattern, having normal FEV and FVC. FIG. 1C illustrates an obstructive pattern. An obstructive pattern occurs when there is airway obstruction from any cause, as in asthma, bronchitis, emphysema, or advanced bronchiectasis; these conditions are grouped together in the nonspecific term chronic obstructive pulmonary disease (COPD). In this pattern, the residual volume is increased and the RV/TLC ratio is markedly increased. Owing to increased airway resistance, the flow rates are decreased. The FEV/FVC ratios, MMFR, and MEFR are all decreased; $FEV_{1.0}$/FVC is less than 75 percent.

FIG. 1D illustrates a restrictive pattern. A restrictive pattern occurs when there is a loss of lung tissue or when lung expansion is limited as a result of decreased compliance of the lung or thorax or of muscular weakness. The conditions in which this pattern can occur include pectus excavatum, myasthenia gravis, diffuse idiopathic interstitial fibrosis, and space occupying lesions (tumors, effusions). In this pattern, the vital capacity and FVC are less than 80 percent of the predicted value, but the FEV/FVC ratios are normal. The TLC is decreased and the RV/TLC ratio is normal.

Embodiments of the invention utilize a patient-external respiratory therapy device to perform periodic pulmonary function testing. A CPAP or other external respiratory device may measure ventalitory pressure, ventilatory airflow, and/or ventalitory gas concentration during periodic, e.g., nightly, therapy sessions. The ventalitory pressure and/or airflow measurements may be used to measure FVC and FEV during forced expiration. From these two parameters, FEV/FVC can be derived to differentiate obstructive versus restrictive respiratory patterns as shown in the FIGS. 1C and 1D. Other measurements that are possible using the respiratory device sensors include low forced expiratory flow (FEF), high functional residual capacity (FRC), total lung capacity (TLC), and high residual volume (RV).

In one embodiment, the patient may perform forced expirations while connected to the external respiratory device. During the forced expirations, circuitry in the external respiratory device may collect measurements, including measurements useful in calculating the FEV and FVC measurements.

In addition, the forced expiratory flow ($FEF_{25-75\%}$) may be measured. The middle half by volume of the total expiration is marked, and its duration is measured. The $FEF_{25-75\%}$ is the volume in liters divided by the time in seconds. In patients with obstructive diseases, the $FEF_{25-75\%}$ is generally greater than their expected values.

Circuitry incorporated in the CPAP device may be used to compare measured FVC, FEV and $FEF_{25-75\%}$ values derived from the respiratory therapy device pressure sensors and/or airflow sensors with predicted values from normal subjects in accordance with various embodiments. The comparison provides diagnostic information of lung mechanics. Data acquired by the CPAP device may be transmitted, for example, from the respiratory therapy device to an advanced patient management (APM) system or other remote device.

The results of pulmonary function testing, along with other physiological conditions measured by the CPAP and/or other devices of the system, may be compared to initial or baseline results to detect changes and/or determine trends in the patient's cardiopulmonary status over time. The changes from baseline values may be used to discern a presence of disease processes. Further, over time, a database of information about relevant conditions and specific to the patient is established. The information may be used to develop sets of criteria specific to the patient and associated with the presence of a particular cardiac and/or pulmonary disease processes. Thus, in some implementations, the system may learn to recognize the presence of disease based on the history of symptoms and/or physiological changes that occur in a particular patient.

In some embodiments, pulmonary function testing may be performed using a cardiac rhythm management system (CRM) or other implantable device. In one implementation, the pulmonary function testing is performed using an implanted transthoracic impedance sensor. Transthoracic impedance sensing has been used in connection with rate-adaptive pacemakers to measure respiration cycles. An impedance sensor may be used to measure the variation in transthoracic impedance, which increases during the inspiratory and decreases during the expiratory phase of a respiration cycle. The sensor injects a sub-threshold stimulating current between the pacemaker case and an electrode on an intracardiac or subcutaneous lead, and measures the voltage across the case and another electrode on the same or another lead. Clinical investigations have shown that the impedance sensor can measure respiratory rate tidal volume, and minute ventilation accurately.

In accordance with various embodiments of the invention, a properly calibrated impedance sensor, implemented in cooperation with a pacemaker or other implantable device, may be used to measure FVC and FEV during forced expiration. From these two parameters, FEV/FVC can be derived to differentiate obstructive versus restrictive respiratory patterns as shown in the FIGS. 1C and 1D, respectively.

In addition, the forced expiratory flow ($FEF_{25-75\%}$) may be measured. The middle half by volume of the total expiration is marked, and its duration is measured. The $FEF_{25-75\%}$ is the volume in liters divided by the time in seconds. In patients with obstructive diseases, the $FEF_{25-75\%}$ is generally greater than their expected values.

The implantable device may be used to compare measured FVC, FEV and $FEF_{25-75\%}$ values derived from the implanted impedance sensor with predicted values from normal subjects in accordance with various embodiments. The comparison provides diagnostic information of lung mechanics.

Data acquired using the above-described techniques may be transmitted from the implantable device to an advanced patient management system or other remote device. Assessment of the patient's cardiopulmonary status or control of the therapy may be performed by the advanced patient management system.

Methods and systems for acquiring and using pulmonary function testing information, aspects of which may be utilized in connection with embodiments of the invention, are described in commonly owned U.S. Pat. No. 7,329,226, which is incorporated herein by reference.

Figure 1E:
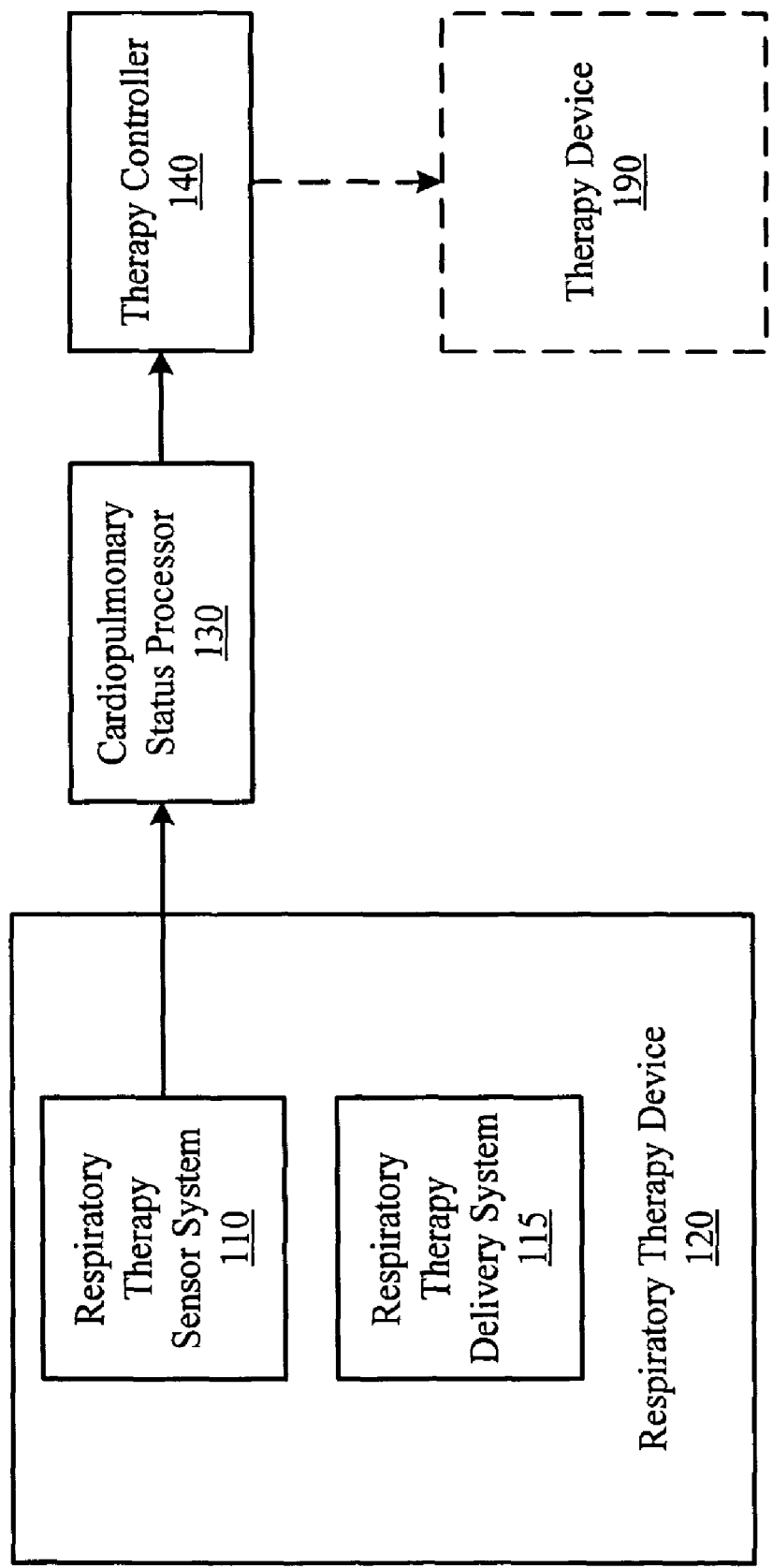
FIGS. 1E and 1F are block diagrams of medical systems that may be used to implement therapy control based on cardiopulmonary status assessment in accordance with embodiments of the invention.
Figure 1F:
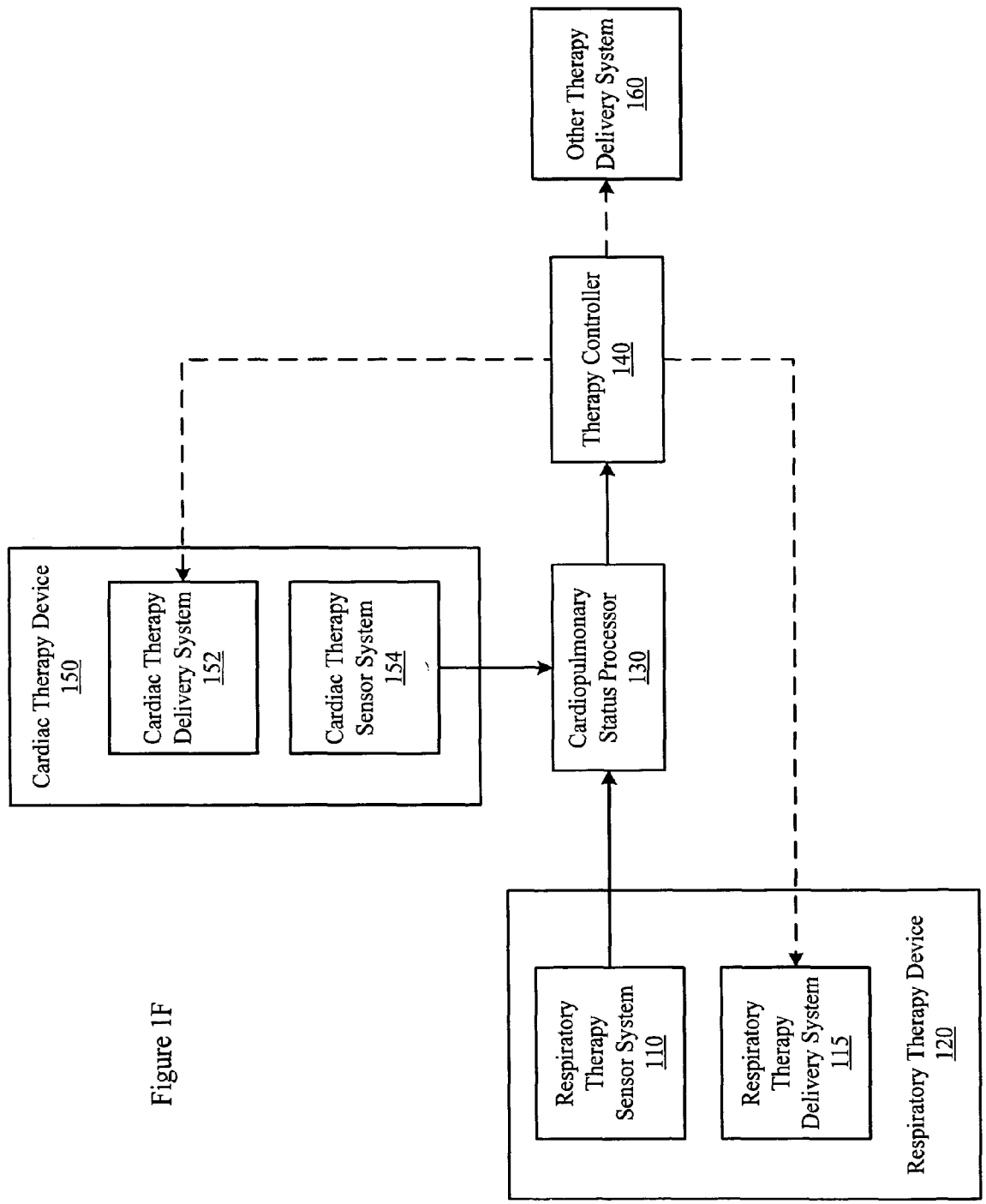

FIGS. 1E and 1F are block diagrams of medical systems that may be used to implement therapy control based on cardiopulmonary status assessment in accordance with embodiments of the invention. In these embodiments, the system utilizes a sensor system 110 of a respiratory therapy device 120 to sense one or more physiological conditions. For example, the sensor system 110 may sense conditions associated with patient respiration, including breathing cycles, respiratory pressure, concentration of respiratory gases, respiratory airflow, and/or other physiological conditions. The respiratory therapy device 110 includes a respiratory therapy delivery system 115, such as a positive airway pressure delivery system in the case of a CPAP device, for example.

Figure 6A:
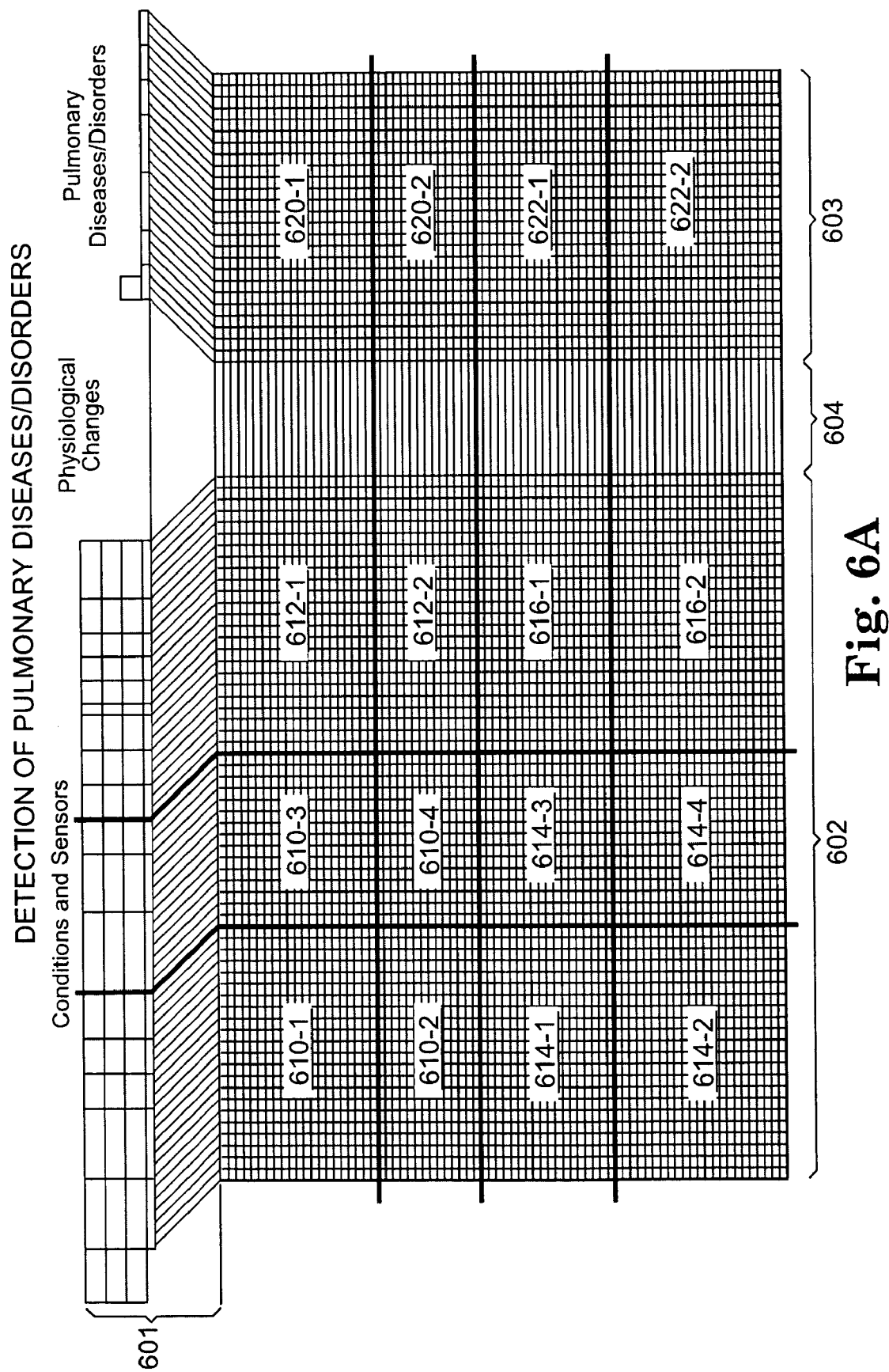
FIGS. 6A-6N illustrate a chart depicting relationships between pulmonary diseases, symptoms and/or physiological changes caused by the pulmonary diseases, and conditions used to detect the symptoms and/or physiological changes that may be used to assess cardiopulmonary status and/or detect a presence of cardiopulmonary disease in accordance with embodiments of the invention.

The system includes a cardiopulmonary status processor 130 coupled to the respiratory therapy sensor system 110. The cardiopulmonary status processor assesses the patient's cardiopulmonary status. Assessment of cardiopulmonary status may include evaluating the patient's pulmonary function as previously described. In some implementations, the cardiopulmonary status processor may work in cooperation with the respiratory therapy device, and/or other therapy or diagnostic devices to perform the pulmonary function testing required or desired. Cardiopulmonary status evaluation may comprise determining and/or assessing a presence of cardiac and/or pulmonary disease. The charts provided in FIGS. 6A-6N illustrate conditions and sensors that may be used to sense physiological changes associated with various cardiac and/or pulmonary diseases and disorders.

As illustrated in FIG. 1E, the system include a therapy controller 140, that develops control signals that may be used to control one or more therapy devices 160.

FIG. 1F illustrates another embodiment of the invention. The embodiment illustrated in FIG. 1F includes a cardiac therapy device 150 including a cardiac therapy sensor system 154 that is used in combination with the respiratory therapy sensor system 110 to assess the patient's cardiopulmonary status. Signals from the cardiac therapy sensor system 154 and the respiratory therapy system 115 are utilized by the cardiopulmonary status processor 130 to determine the cardiopulmonary status of the patient. Assessment of the patient's cardiopulmonary status may involve sensing a presence of a cardiac and/or pulmonary disease. The sensor systems 110, 154, of one or both of the respiratory therapy device 120, the cardiac therapy device 154, and/or other sensor systems (not shown), may be used for cardiopulmonary status assessment.

The sensor systems 110, 154, may be used in connection with performing pulmonary function testing as described above. Cardiopulmonary status assessment may comprise determining and/or assessing a presence of cardiac and/or pulmonary disease. The charts provided in FIGS. 6A-6N illustrate conditions and sensors that may be used to sense physiological changes associated with various cardiac and/or pulmonary diseases and disorders. According to one aspect of the invention, the cardiopulmonary status processor may assess a presence of a cardiac disease/disorder. The cardiac disease/disorder assessment may involve, for example, cardiac rhythm related disorders, arterial diseases, heart failure, and/or hypertension.

The cardiopulmonary status processor may be used to detect a presence of one or more rhythm-related and/or non-rhythm related pulmonary diseases/disorders. Rhythm-related breathing disorders involve disruption of the normal respiratory cycle. Although disordered breathing often occurs during sleep, the condition may also occur while the patient is awake.

Breathing rhythm disorders may include, for example, apnea, hypopnea, Cheyne-Stokes respiration, periodic breathing, as indicated in the charts of FIGS. 6A-6N, and/or other disorders manifested by disruption of normal breathing cycles. Apnea is a fairly common disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration cycles have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes respiration (CSR). Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiopulmonary implications, detection and therapy for disordered breathing is of particular interest.

Disordered breathing may be detected by sensing and analyzing various conditions associated with disordered breathing. Table 1 provides examples of how a representative subset of physiological and non-physiological, contextual conditions may be used in connection with disordered breathing detection.

TABLE 1

| Condition Type | Condition | Examples of how condition may be used in disordered breathing detection |
|---|---|---|
| Physiological | Heart rate | Decrease in heart rate may indicate disordered breathing episode. Increase in heart rate may indicate autonomic arousal from a disordered breathing episode. Decrease in heart rate may indicate the patient is asleep. |
| | Heart rate variability | Disordered breathing causes heart rate variability to decrease. Changes in HRV associated with sleep disordered breathing may be observed while the patient is awake or asleep |
| | Ventricular filling pressure | May be used to identify/predict pulmonary congestion associated with respiratory disturbance. |
| | Blood pressure | Swings in on-line blood pressure measures are associated with apnea. Disordered breathing generally increases blood pressure variability - |

TABLE 1-continued

| Condition Type | Condition | Examples of how condition may be used in disordered breathing detection |
|---|---|---|
| | | these changes may be observed while the patient is awake or asleep. |
| | Snoring | Snoring is associated with a higher incidence of obstructive sleep apnea and may be used to detect disordered breathing. |
| | Respiration pattern/rate | Respiration patterns including, e.g., respiration rate, may be used to detect disordered breathing episodes. Respiration patterns may be used to determine the type of disordered breathing. Respiration patterns may be used to detect that the patient is asleep. |
| | Patency of upper airway | Patency of upper airway is related to obstructive sleep apnea and may be used to detect episodes of obstructive sleep apnea. |
| | Pulmonary congestion | Pulmonary congestion is associated with respiratory disturbances. |
| | Sympathetic nerve activity | End of apnea associated with a spike in SNA. Changes in SNA observed while the patient is awake or asleep may be associated with sleep disordered breathing |
| | $CO_2$ | Low $CO_2$ levels initiate central apnea. |
| | $O_2$ | $O_2$ desaturation occurs during severe apnea/hypopnea episodes. |
| | Blood alcohol content | Alcohol tends to increase incidence of snoring & obstructive apnea. |
| | Adrenalin | End of apnea associated with a spike in blood adrenaline. |
| | BNP | A marker of heart failure status, which is associated with Cheyne-Stokes Respiration |
| | C-Reactive Protein | A measure of inflammation that may be related to apnea. |
| | Drug/Medication/ Tobacco use | These substances may affect the incidence of both central & obstructive apnea. |
| | Muscle atonia | Muscle atonia may be used to detect REM and non-REM sleep. |
| | Eye movement | Eye movement may be used to detect REM and non-REM sleep. |
| Non-physiological | Temperature | Ambient temperature may be a condition predisposing the patient to episodes of disordered breathing and may be useful in disordered breathing detection. |
| | Humidity | Humidity may be a condition predisposing the patient to episodes of disordered breathing and may be useful in disordered breathing detection. |
| | Pollution | Pollution may be a condition predisposing the patient to episodes of disordered breathing and may be useful in disordered breathing detection. |
| | Posture | Posture may be used to confirm or determine the patient is asleep. |
| | Activity | Patient activity may be used in relation to sleep detection. |
| | Location | Patient location may used to determine if the patient is in bed as a part of sleep detection. |
| | Altitude | Lower oxygen concentrations at higher altitudes tends to cause more central apnea |

In one embodiment, episodes of disordered breathing may be detected by monitoring the respiratory waveform output of a transthoracic impedance sensor. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

In various embodiments, episodes of disordered breathing may be detected by analyzing the patient's respiratory cycles. For example, the patient's respiration cycles may be detected using a transthoracic impedance sensor, external respiratory bands, or other sensor configured to sense a signal modulated by patient respiration. A respiration cycle may be divided into an inspiration period corresponding to the patient inhaling, an expiration period, corresponding to the patient exhaling, and a non-breathing period occurring between inhaling and exhaling. Respiration intervals are established using inspiration and expiration thresholds. The inspiration threshold marks the beginning of an inspiration period and may be determined by the sensor signal rising above the inspiration threshold. The respiration cycle may be determined to transition from an inspiration period to an expiration period when the sensor signal is maximum. The expiration interval continues until the sensor signal falls below an expiration threshold. A non-breathing interval starts from the end of the expiration period and continues until the beginning of the next inspiration period.

Detection of apnea and severe apnea according to embodiments of the invention may be accomplished based on the length of the patient's non-breathing periods. A condition of apnea is detected when a non-breathing period exceeds a first predetermined interval, denoted the apnea interval. A condition of severe apnea is detected when the non-breathing period exceeds a second predetermined interval, denoted the severe apnea interval. For example, apnea may be detected when the non-breathing interval exceeds about 10 seconds, and severe apnea may be detected when the non-breathing interval exceeds about 20 seconds. Methods and systems for detecting breathing rhythm disorders, aspects of which may be utilized in connection with a therapy control system described herein, are described in commonly owned U.S. Pat. No. 7,252,640, which is incorporated herein by reference.

Detection of apnea and severe apnea may utilize information related to the patient's sleep state. Because disordered breathing occurs more frequently during sleep, assessment of rhythm-related breathing disorders may involve determination of whether the patient is asleep. Other types of cardiopulmonary disorders may be modified by the patient's sleep state. The cardiopulmonary status processor may use sleep state information in connection with the assessment of the patient's cardiopulmonary status. Methods and systems for sleep and/or sleep stage detection, aspects of which may be utilized in connection with a therapy control system described herein, are described in commonly owned U.S. Pat. No. 7,189,204, and U.S. Publication No. 2005/0043652, which are incorporated herein by reference.

The cardiopulmonary status processor 130 develops signals related to the patient's cardiopulmonary status. These signals are transmitted to a therapy controller 140 that utilizes signals to control therapy delivered to the patient. The controlled therapy may comprise a respiratory therapy delivered to the patient by a respiratory therapy delivery system 115, a cardiac therapy delivered to the patient by a cardiac therapy delivery system 152, or a therapy delivered by another therapy system 160, e.g., internal or external nerve or muscle stimulator and/or internal or external drug pump. Various methods and systems for implementing cardiac therapy to treat disordered breathing are described in commonly owned U.S. Pat. No. 7,720,541, which is incorporated herein by reference.

Figure 2:
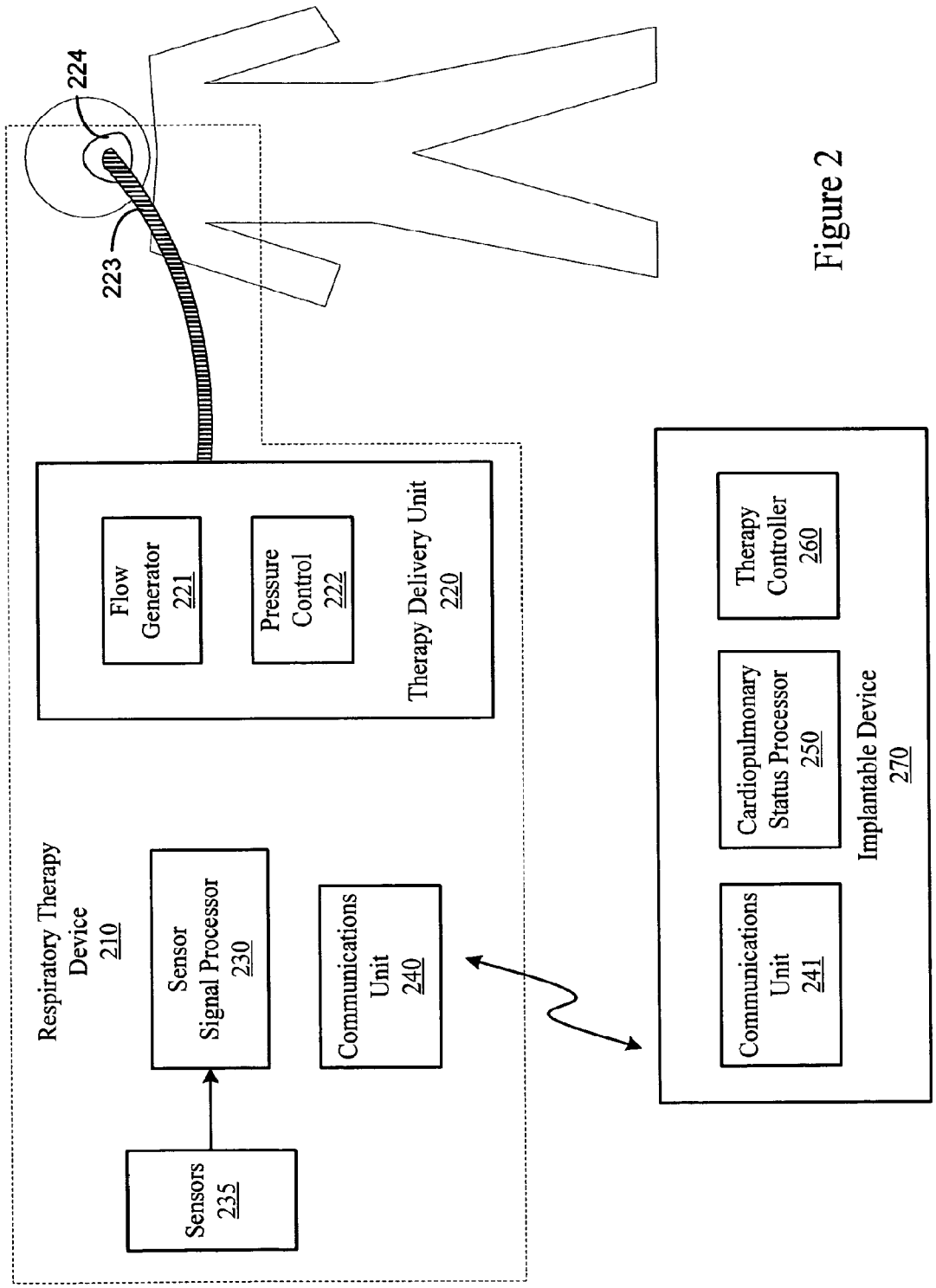
FIG. 2 illustrates a medical system including an external respiratory device and an implantable device that may be used to assess the patient's cardiopulmonary status and control the delivery of therapy in accordance with embodiments of the invention.

FIG. 2 illustrates a block diagram of a therapy system including a respiratory therapy device 210, e.g., CPAP device or other respiratory therapy device, which may be used to provide external respiratory therapy for disordered breathing. The respiratory therapy device 210 includes one or more sensors 235, e.g., flow, pressure and/or exhaled gas concentration sensors used to sense respiratory conditions and/or other conditions useful in the assessment of the patient's cardiopulmonary status. Signals generated by the sensors 235 are processed by signal processing circuitry 230 within the respiratory therapy device 210.

The respiratory therapy device 210 may comprise any of the patient-external respiratory therapy devices, including CPAP, bi-level positive airway pressure (bi-PAP), proportional positive airway pressure (PPAP), and/or autotitration positive airway pressure devices, for example. It is understood that a portion of a patient-external respiratory therapy device 210 may be positioned within an orifice of the body, such as the nasal cavity or mouth, yet can be considered external to the patient.

Continuous positive airway pressure (CPAP) devices deliver a set air pressure to the patient. The pressure level for the individual patient may be determined during a titration study. Such a study may take place in a sleep lab, and involves determination of the optimum airway pressure by a sleep physician or other professional. The CPAP device pressure control is set to the determined level. When the patient uses the CPAP device, a substantially constant airway pressure level is maintained by the device.

Autotitration PAP devices are similar to CPAP devices, however, the pressure controller for autotitration devices automatically determines the air pressure for the patient. Instead of maintaining a constant pressure, the autotitration PAP device evaluates sensor signals and the changing needs of the patient to deliver a variable positive airway pressure. Autotitration PAP and CPAP are often used to treat sleep disordered breathing, for example.

Bi-level positive airway pressure (bi-PAP) devices provide two levels of positive airway pressure. A higher pressure is maintained while the patient inhales. The device switches to a lower pressure during expiration. Bi-PAP devices are used to treat a variety of respiratory dysfunctions, including chronic obstructive pulmonary disease (COPD), respiratory insufficiency, and ALS or Lou Gehrig's disease, among others.

The respiratory therapy device 210 may include a device that provides positive and negative airflow pressure to the patient. Respiratory therapy, including sleep disordered breathing therapy, may be provided by a servo ventilation device. Servo ventilation devices provide airway pressure dependent on the respiration cycle stage. A servo ventilation device provides positive pressure on inhalation and negative pressure on exhalation.

The breathing therapy delivery unit 220 includes a flow generator 221 that pulls in air through a filter. The flow generator 221 is controlled by the pressure control circuitry 222 to deliver an appropriate air pressure to the patient. Air flows through tubing 223 and is delivered to the patient's airway through a mask 224. In one example, the mask 224 may be a nasal mask covering only the patient's nose. In another example, the mask 224 covers the patient's nose and mouth.

The respiratory therapy device 210 may include a communications unit 240 for communicating with a compatible communications unit 241 of one or more separate devices, such as an implantable device 270. In one example, the respiratory therapy device 210 sends information about sensed respiratory flow, pressure, and expired gas to the implantable device. The respiratory therapy device receives therapy control information controlling the therapy delivered by the respiratory therapy device 210 from the implantable device 270.

The implantable device 270, which may comprise an implantable cardiac device, includes a cardiopulmonary status processor 250 used to assess the cardiopulmonary status of the patient. The cardiopulmonary status processor 250 uses the sensor information transferred to the implantable device 270 from the respiratory therapy device 210 to determine the status of the patient's cardiopulmonary system. Information from the respiratory therapy device sensors 235 may be transferred from the respiratory therapy device 210 to the implantable device 270 through communications units 240, 241 of the respective devices 210, 270. In some embodiments, the cardiopulmonary assessment processor 250 may use information acquired by the respiratory therapy device sensors 235 in addition to other information received from other devices and/or sensors in performing the cardiopulmonary status assessment.

The implantable device 270 may additionally or alternatively include a therapy controller 260 that develops therapy control signals based on the patient's assessed cardiopulmonary status. Therapy control signals developed by the therapy controller 260 may be transmitted to the respiratory therapy device 210 through the communications units 241, 240. The therapy control signals are used to control the therapy delivered by the respiratory therapy device. For example, if the cardiopulmonary assessment processor 250 detects a presence of a cardiopulmonary disease, the delivery of respiratory therapy to the patient may be controlled to treat the detected cardiopulmonary disease presence. In other examples, delivery of the respiratory therapy may be controlled to improve patient comfort based on the assessed cardiopulmonary status, or to meet other therapeutic goals.

The therapy controller 260 may control the respiratory therapy by initiating, terminating or modifying the respiratory therapy. Controlling the respiratory therapy may involve initiating, terminating or modifying one or more therapy parameters. For example, the therapy controller 260 may be used to modify gas pressure or gas flow delivered by the respiratory therapy device 210. The therapy controller 260 may initiate or terminate a gas flow or modify a gas concentration of the respiratory therapy, for example.

Additionally or alternatively, the therapy controller 260 may develop control signals used to control therapy delivered by the implantable device 270. The implantable device therapy may be controlled to treat a detected cardiopulmonary disease or disorder, to improve patient comfort, or for other purposes. In one embodiment, the implantable device comprises a cardiac therapy device that delivers cardiac electrical stimulation therapy to the patient. The therapy controller initiate or terminate the cardiac electrical stimulation therapy and/or control various parameters of the cardiac electrical stimulation, e.g., stimulation energy, stimulation timing. The cardiac electrical stimulation therapy may involve non-excitatory electrical stimulation involving sub-capture threshold stimulation or stimulation during a refractory period, for example. The therapy controller may modify one or more parameters of the non-excitatory electrical stimulation therapy.

The cardiac electrical stimulation may involve cardiac pacing therapy. The therapy controller may initiate or terminate the pacing therapy. The therapy controller may modify the cardiac pacing therapy by alter a pacing rate (e.g., change from a normal sleep rate to an overdrive pacing rate), pacing timing (e.g., modify the AV delay or other pacing timing parameter), pacing mode, (e.g., switch from DDD to VVI pacing or from a tracking mode to a non-tracking pacing mode) and/or pacing type (e.g., switch from dual chamber to biventricular pacing or from single chamber to dual chamber).

Figure 3:
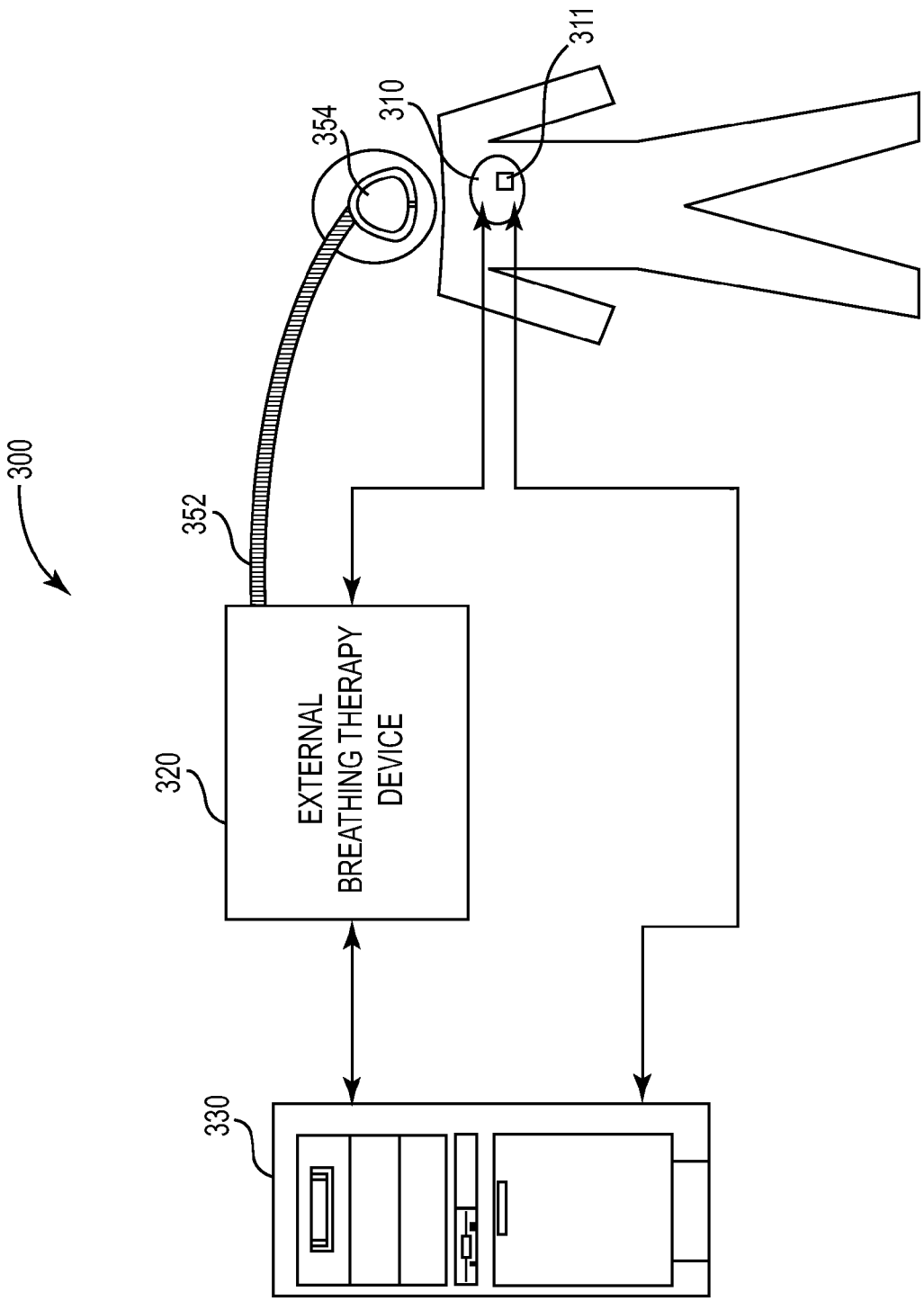
FIG. 3 illustrates a medical system including an external respiratory device and a cardiac rhythm management device that may be used to assess the patient's cardiopulmonary status and control the delivery of therapy in accordance with embodiments of the invention.

FIG. 3 illustrates a system for implementing therapy control based on cardiopulmonary status in accordance with embodiments of the invention. According to the embodiment illustrated in FIG. 3, a medical system 300 includes an implantable cardiac rhythm management (CRM) device 310 that cooperates with a patient-external respiratory therapy device 320 to provide therapy control based on cardiopulmonary status. The CRM device 310 may provide a first set of monitoring, diagnostic or therapeutic functions to the patient. The CRM device 310 may be electrically coupled to the patient's heart 340 through electrodes positioned in, on or about the heart. The cardiac electrodes may sense cardiac electrical signals produced by the heart and/or may provide therapy in the form of electrical stimulation pulses to one or more heart chambers. For example, the cardiac electrodes may deliver electrical stimulation to one or more heart chambers and/or to one or multiple sites within the heart chambers. The CRM device 310 may deliver a variety of cardiac therapies, such as cardiac pacing, defibrillation, cardioversion, cardiac resynchronization, and/or other cardiac therapies, for example. In addition, the CRM device 310 may facilitate control of the external respiratory device 320.

The CRM device 310 includes a cardiopulmonary assessment processor and therapy controller 311 disposed within the housing of the CRM device 310. The cardiopulmonary assessment processor and therapy controller 311 utilizes physiological signals sensed by an external respiratory therapy device 320 to assess a cardiopulmonary status of the patient and to develop control signals to control the therapy delivered by the respiratory therapy device 320, the CRM device 310 or both devices 310, 320.

In the example illustrated in FIG. 3, the external respiratory therapy device 320 comprises a continuous positive airway pressure (CPAP) device. The CPAP device develops a positive air pressure that is delivered to the patient's airway through tubing 352 and mask 354. CPAP device are often used to treat disordered breathing. In one configuration, for example, the positive airway pressure provided by the CPAP device 320 acts as a pneumatic splint keeping the patient's airway open and reducing the severity and/or number of occurrences of disordered breathing due to airway obstruction.

In addition to the therapy described above, the CPAP device 320 may provide a number of monitoring, and/or diagnostic functions in relation to the patient's cardiopulmonary system. Physiological signals sensed by the sensor system of the CPAP device 320 may be used to assess the patient's cardiopulmonary status. Therapy delivered by the CPAP device 320, the CRM device 310, and/or other therapy devices may be controlled based on the patient's cardiopulmonary status.

In one implementation, the therapy controller 311 may signal one or both of the respiratory therapy device 320 and the cardiac therapy device 310 to initiate, terminate or modify the therapy delivered by the respective devices. The therapy controller 311 may be programmed to recognize and respond to various changes in cardiopulmonary status based on the conditions sensed by the sensing systems of the respiratory therapy device 320 and/or the cardiac therapy device 310.

For example, the therapy controller 311 may compare the cardiopulmonary status of the patient derived from the sensed conditions to a cardiopulmonary status criteria stored in the therapy controller 311. The therapy controller 311 may include decision logic that determines if therapy changes are indicated based on the comparison of the determined cardiopulmonary status to the cardiopulmonary criteria.

The CRM device 310 and the CPAP device 320 may communicate directly through a wireless communication link, for example. Alternatively, or additionally, the CRM device 310 and the CPAP device 320 may be coupled via a wireless or wired communications link, for example, to a separate device such as a patient information server 330 that is part of an advanced patient management (APM) system. The APM patient information server 330 may be used to facilitate communication between the medical devices 310, 320. The APM patient information server 330 may be used, for example, to download and store data collected by the CRM device 310 and/or the CPAP device 320.

Data stored on the APM patient management server 330 may be accessible by the patient and/or the patient's physician through terminals, e.g., remote terminals located in the patient's home or physician's office. The APM patient information server 330 may be used to communicate to one or more of the medical devices 310, 320 to facilitate control of the monitoring, diagnostic and/or therapeutic functions of the devices 310, 320. Systems and methods involving advanced patient management systems, aspects of which may be incorporated in connection with therapy control based on cardiopulmonary status as in accordance with embodiments presented herein, are described in U.S. Pat. Nos. 6,336,903, 6,312,378, 6,270,457, and 6,398,728 which are incorporated herein by reference.

In one embodiment, the CRM device 310 and the CPAP device 320 do not communicate directly, but may communicate indirectly through the APM server 330. In this embodiment, the APM system 330 operates as an intermediary between two or more medical devices 310, 320. For example, sensor information relevant to the assessment of the patient's cardiopulmonary status may be transferred from the CPAP device 320 to the APM system 330. The APM system 330 may then transfer the sensor information to the CRM device 310 for use in cardiopulmonary status assessment. The CRM device 310 may transfer respiratory therapy control information from the CRM device 310 to the APM system 330. The APM system 330 may then transfer the respiratory therapy control information to the CPAP device 320.

Although FIG. 3 illustrates a system comprising a CRM device 310 used with a CPAP device 320 to provide therapy controlled by the patient's cardiopulmonary status, any number of patient-internal and/or patient-external devices may be included in the system 300. For example, a drug delivery device, such as a drug pump or controllable nebulizer, may be included in the system 300. The drug delivery device, or other device, may include sensors that sense conditions used to assess the patient's cardiopulmonary status. The drug delivery device, or other device, may deliver a therapy controlled based on the patient's assessed cardiopulmonary status.

Figure 4:
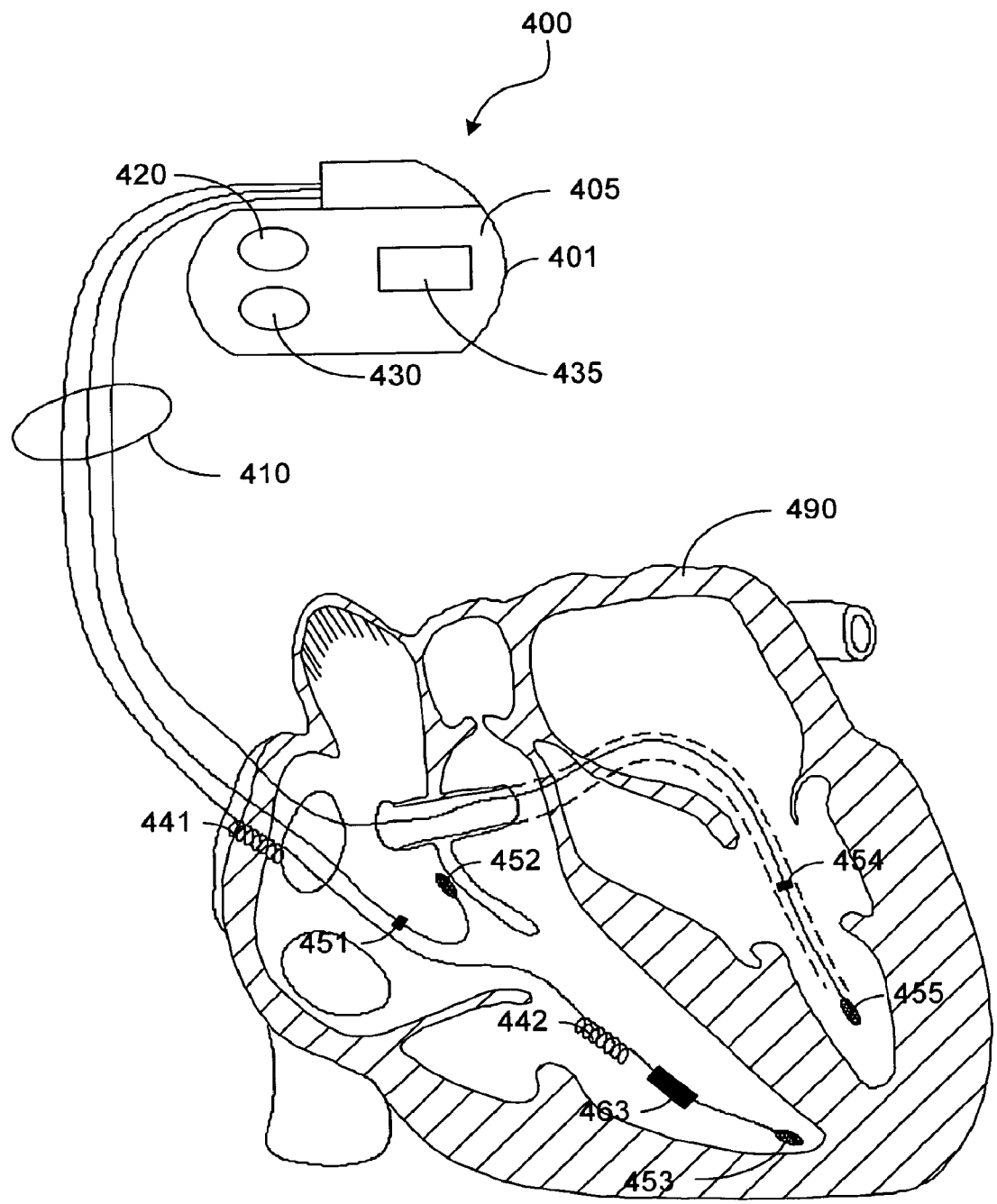
FIGS. 4 and 5 are partial views of implantable cardiac devices that may be used for cardiopulmonary status assessment and therapy control in accordance with embodiments of the invention.

FIG. 4 is a partial view of an implantable device that may include circuitry for implementing therapy control based on cardiopulmonary status in accordance with embodiments of the invention. In this example, the cardiopulmonary status processor 435 the implantable is configured as a component of a pulse generator 405 of a cardiac rhythm management device (CRM) 400. The cardiopulmonary status processor 435 includes an interface for receiving signals from a sensor system of a patient-external respiratory therapy device. Additionally, the cardiopulmonary status processor 435 may receive signals from one or more sensors of the CRM. In some embodiments, a therapy controller may be additionally configured as a component of the cardiac rhythm management device 400. The cardiopulmonary status processor 435 and/or the therapy controller may alternatively be implemented in a variety of implantable monitoring, diagnostic, and/or therapeutic devices, such as an implantable cardiac monitoring device, an implantable drug delivery device, or an implantable neurostimulation device, for example.

The implantable pulse generator 405 is electrically and physically coupled to an intracardiac lead system 410. Portions of the intracardiac lead system 410 are inserted into the patient's heart 490. The intracardiac lead system 410 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 401 of the pulse generator 405 may optionally serve as a can electrode.

Communications circuitry is disposed within the housing 401, facilitating communication between the pulse generator 405 including the cardiopulmonary status processor 435 and another device or system, such as the sensing system of a respiratory therapy device and/or APM system. The communications circuitry can also facilitate unidirectional or bidirectional communication with one or more implanted, external, cutaneous, or subcutaneous physiologic or non-physiologic sensors, patient-input devices and/or information systems.

The pulse generator 405 may optionally incorporate an activity sensor 420. The activity sensor may be configured, for example, to sense patient activity. Patient activity may be used in connection, for example, with rate adaptive pacing, and/or sleep detection. The motion sensor 420 may be implemented as an accelerometer positioned in or on the housing 401 of the pulse generator 405. If the motion sensor 420 is implemented as an accelerometer, the motion sensor 420 may also provide acoustic information, e.g. rales, coughing, S1-S4 heart sounds, cardiac murmurs, and other acoustic information.

The lead system 410 of the CRM 400 may incorporate a transthoracic impedance sensor that may be used to acquire the patient's respiration waveform, or other respiration-related information. The transthoracic impedance sensor may include, for example, one or more intracardiac electrodes 441, 442, 451-455, 463 positioned in one or more chambers of the heart 490. The intracardiac electrodes 441, 442, 451-455, 463 may be coupled to impedance drive/sense circuitry 430 positioned within the housing of the pulse generator 405.

In one implementation, impedance drive/sense circuitry 430 generates a current that flows through the tissue between an impedance drive electrode 451 and a can electrode on the housing 401 of the pulse generator 405. The voltage at an impedance sense electrode 452 relative to the can electrode changes as the patient's transthoracic impedance changes. The voltage signal developed between the impedance sense electrode 452 and the can electrode is detected by the impedance sense circuitry 430. Other locations and/or combinations of impedance sense and drive electrodes are also possible. The impedance signal may also be used to detect other physiological changes besides respiration that result in a change in impedance, including pulmonary edema, heart size, cardiac pump function, etc. The respiratory and/or pacemaker therapy may be altered on the basis of the patient's heart condition as sensed by impedance.

Figure 7:
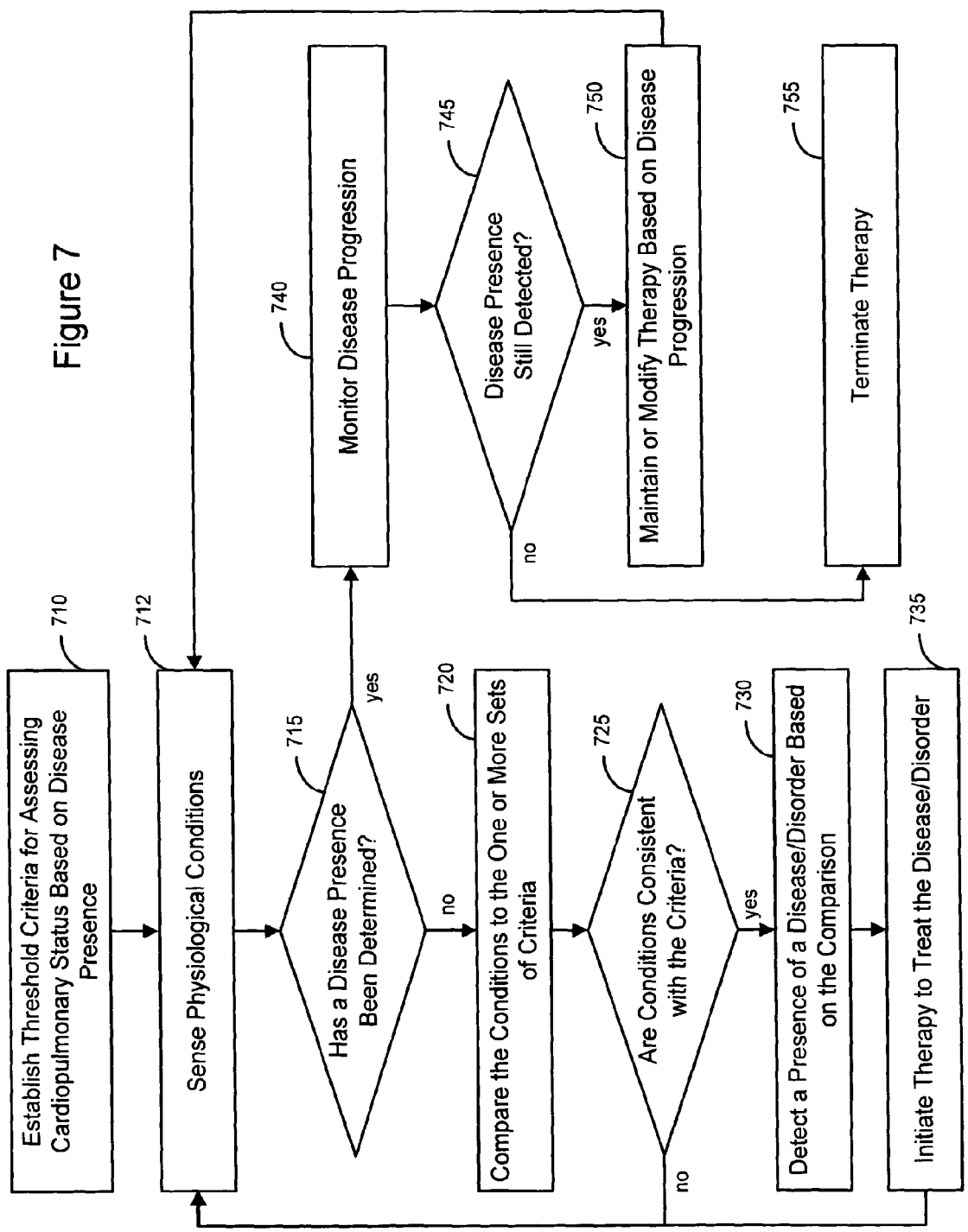
FIG. 7 is a flowchart illustrating a method of assessing a presence of a non-rhythm pulmonary disease and delivering drug therapy in accordance with embodiments of the invention.

The voltage signal developed at the impedance sense electrode 452 is proportional to the patient's transthoracic impedance and represents the patient's respiration waveform. The transthoracic impedance increases during respiratory inspiration and decreases during respiratory expiration. The transthoracic impedance may be used to determine the amount of air moved in one breath, denoted the tidal volume and/or the amount of air moved per minute, denoted the minute ventilation. A normal "at rest" respiration pattern, e.g., during non-REM sleep, includes regular, rhythmic inspiration—expiration cycles without substantial interruptions, as indicated in FIG. 7.

Returning to FIG. 4, the lead system 410 may include one or more cardiac pace/sense electrodes 451-455 positioned in, on, or about one or more heart chambers for sensing electrical signals from the patient's heart 490 and/or delivering pacing pulses to the heart 490. The intracardiac sense/pace electrodes 451-455, such as those illustrated in FIG. 4, may be used to sense and/or pace one or more chambers of the heart, including the left ventricle, the right ventricle, the left atrium and/or the right atrium. The lead system 410 may include one or more defibrillation electrodes 441, 442 for delivering defibrillation/cardioversion shocks to the heart.

The pulse generator 405 may include circuitry for detecting cardiac arrhythmias and/or for controlling pacing or defibrillation therapy in the form of electrical stimulation pulses or shocks delivered to the heart through the lead system 410. The cardiopulmonary status processor 435 may be disposed within the housing 401 of the pulse generator 405. The cardiopulmonary status processor 435 may be coupled to various sensors, including the transthoracic impedance sensor 430 and activity sensor 420, patient-external respiration therapy device and/or systems or devices through leads or through wireless communication links.

The cardiopulmonary status processor 435 may be coupled to a therapy control unit configured to develop control information for therapy delivered to the patient based on the patient's cardiopulmonary status. In one embodiment, the therapy controller may also be configured as a component of the pulse generator 405 and may be positioned within the pulse generator housing 401. In another embodiment, the therapy controller may be positioned outside the pulse generator housing 401 and communicatively coupled to the cardiopulmonary status processor 435, e.g., through a wireless communications link.

Figure 5:
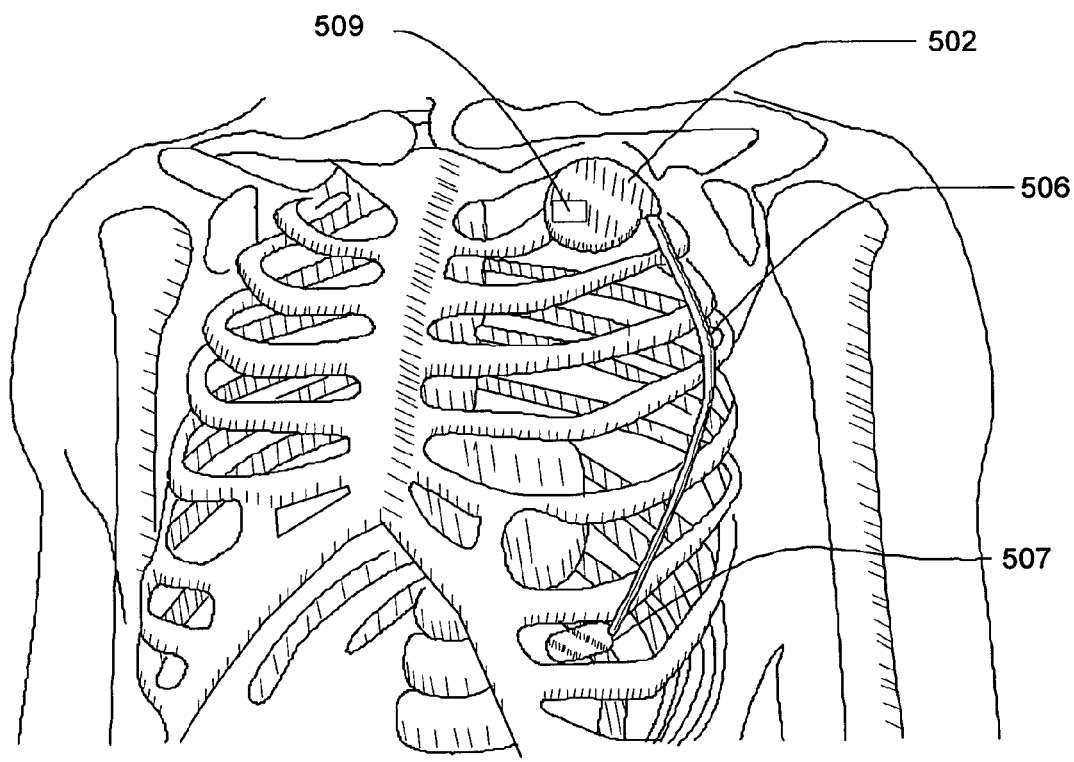

FIG. 5 is a diagram illustrating an implantable transthoracic cardiac device that may be used in connection with therapy control based on cardiopulmonary status in accordance with embodiments of the invention. The implantable device illustrated in FIG. 5 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

Circuitry for implementing a cardiopulmonary status processor or cardiopulmonary status processor and a therapy controller may be positioned within the primary housing of the ITCS device. The primary housing (e.g., the active or non-active can) of the ITCS device, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In the configuration shown in FIG. 5, a subcutaneous electrode assembly 507 can be positioned under the skin in the chest region and situated distal from the housing 502. The subcutaneous and, if applicable, housing electrode(s) can be positioned about the heart at various locations and orientations, such as at various anterior and/or posterior locations relative to the heart. The subcutaneous electrode assembly 507 is coupled to circuitry within the housing 502 via a lead assembly 506. One or more conductors (e.g., coils or cables) are provided within the lead assembly 506 and electrically couple the subcutaneous electrode assembly 507 with circuitry in the housing 502. One or more sense, sense/pace or defibrillation electrodes can be situated on the elongated structure of the electrode support, the housing 502, and/or the distal electrode assembly (shown as subcutaneous electrode assembly 507 in FIG. 5).

It is noted that the electrode and the lead assemblies 507, 506 can be configured to assume a variety of shapes. For example, the lead assembly 506 can have a wedge, chevron, flattened oval, or a ribbon shape, and the subcutaneous electrode assembly 507 can comprise a number of spaced electrodes, such as an array or band of electrodes. Moreover, two or more subcutaneous electrode assemblies 507 can be mounted to multiple electrode support assemblies 506 to achieve a desired spaced relationship amongst subcutaneous electrode assemblies 507.

In particular configurations, the ITCS device may perform functions traditionally performed by cardiac rhythm management devices, such as providing various cardiac monitoring, pacing and/or cardioversion/defibrillation functions. Exemplary pacemaker circuitry, structures and functionality, aspects of which can be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations can provide for non-physiologic pacing support in addition to, or to the exclusion of, bradycardia and/or anti-tachycardia pacing therapies. Exemplary cardiac monitoring circuitry, structures and functionality, aspects of which can be incorporated in an ITCS of the present invention, are disclosed in commonly owned U.S. Pat. Nos. 5,313,953; 5,388,578; and 5,411,031, which are hereby incorporated herein by reference in their respective entireties.

An ITCS device can incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243 and commonly owned U.S. Patent Application Ser. No. 60/462,272, filed Apr. 11, 2003, Ser. No. 10/462,001, filed Jun. 13, 2003, now U.S. Publication No. 2004/0230229, Ser. No. 10/465,520, filed Jun. 19, 2003, now U.S. Publication No. 2004/0230230, Ser. No. 10/820,642 filed Apr. 8, 2004, now U.S. Pat. No. 7,570,997, and Ser. No. 10/821,248, filed Apr. 8, 2004, now U.S. Publication No. 2004/0215240, which are incorporated herein by reference.

The housing of the ITCS device may incorporate components of a monitoring unit 409, including a memory, sensor interface, and/or event detector circuitry. The monitoring unit 509 may be coupled to one or more sensors, patient input devices, and/or information systems. In some embodiments, the housing of the ITCS device may also incorporate components of a therapy feedback unit. In other embodiments, circuitry to implement the therapy feedback unit may be configured within a device separate from the ITCS device. In this embodiment, the therapy feedback unit and the monitoring unit may be communicatively coupled using leads or a wireless communication link, for example.

In one implementation, the ITCS device may include an impedance sensor configured to sense the patient's transthoracic impedance. The impedance sensor may include the impedance drive/sense circuitry incorporated with the housing 502 of the ITCS device and coupled to impedance electrodes positioned on the can or at other locations of the ITCS device, such as on the subcutaneous electrode assembly 507 and/or lead assembly 506. In one configuration, the impedance drive circuitry generates a current that flows between a subcutaneous impedance drive electrode and a can electrode on the primary housing of the ITCS device. The voltage at a subcutaneous impedance sense electrode relative to the can electrode changes as the patient's transthoracic impedance changes. The voltage signal developed between the impedance sense electrode and the can electrode is sensed by the impedance drive/sense circuitry.

Communications circuitry is disposed within the housing 502 for facilitating communication between the ITCS device, including the cardiopulmonary status processor 509, and an external communication device, such as a portable or bedside communication station, patient-carried/worn communication station, or external programmer, for example. The communications circuitry facilitates communication of signals developed by a sensing system of a patient-external respiratory therapy device and used by the cardiopulmonary status processor in connection with assessment of the patient's cardiopulmonary status. The communications circuitry can also facilitate unidirectional or bidirectional communication with one or more external, cutaneous, or subcutaneous physiologic or non-physiologic sensors.

Assessment of cardiopulmonary status may include assessing the patient's pulmonary function as previously described. In some implementations, the cardiopulmonary status processor may use sensed conditions acquired by the respiratory therapy device, and/or other therapy or diagnostic devices to assess patient's cardiopulmonary status. Cardiopulmonary status assessment may comprise evaluating a presence of cardiac and/or pulmonary disease. The charts provided in FIGS. 6A-6N illustrate conditions and sensors that may be used to determine physiological changes associated with various cardiac and/or pulmonary diseases and disorders.

The left section 602 of FIG. 6A illustrates various conditions that may be sensed using sensors of a respiratory therapy device (CPAP), a cardiac device (CRM), or an external non-CPAP, non-CRM device. The top section 601 lists various conditions that may be sensed and provides information about sensors used to sense the conditions. The center section 604 of FIG. 6A provides physiological changes and/or symptoms that may be evaluated using the conditions listed in the left section 602. The right section 603 of FIG. 6A provides pulmonary diseases/disorders. The presence of the pulmonary diseases/disorders of the right section 603 may be assessed based on the physiological changes and/or symptoms of the center section 604.

Figures 1, 6B:
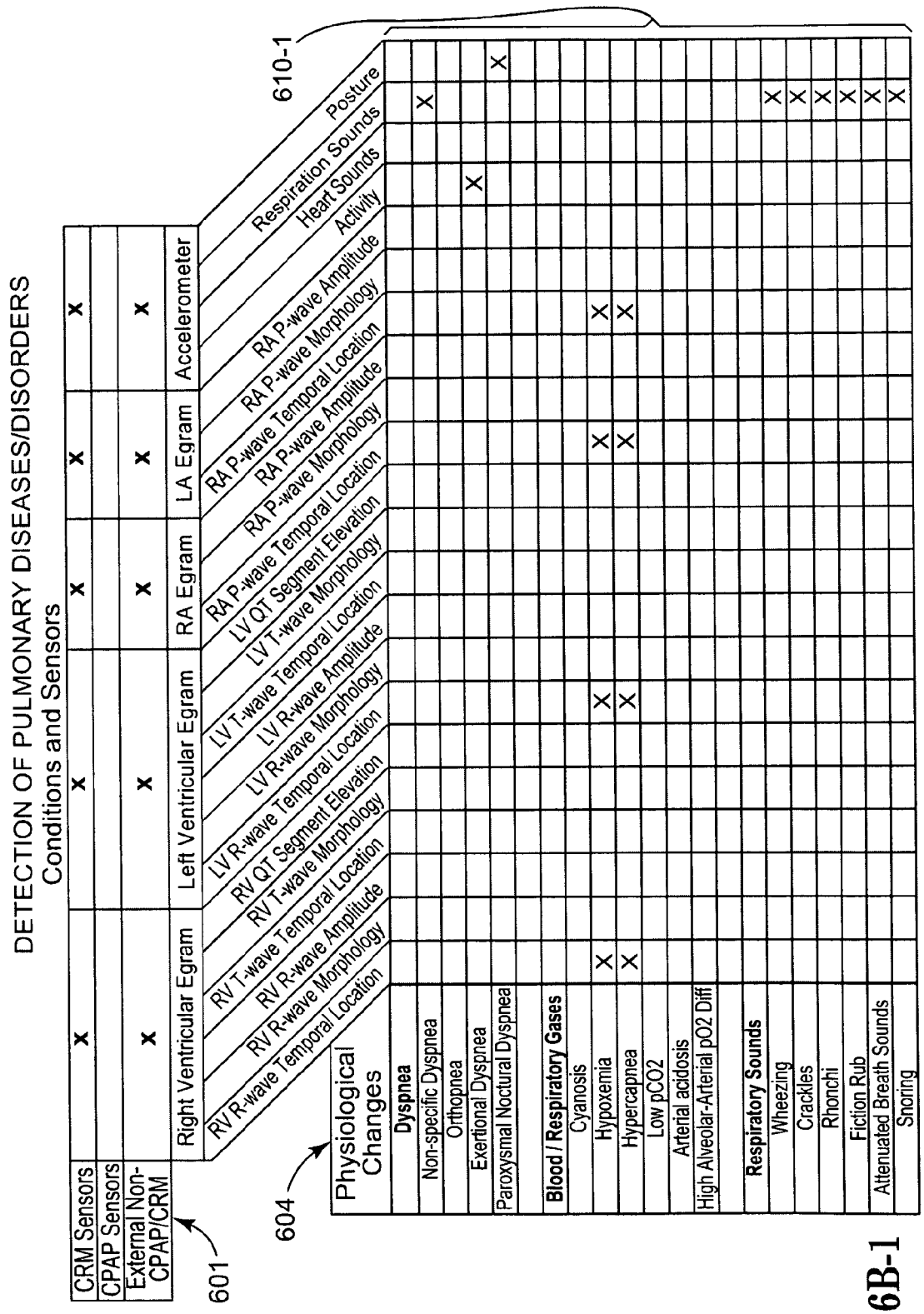
Figures 3, 6B:
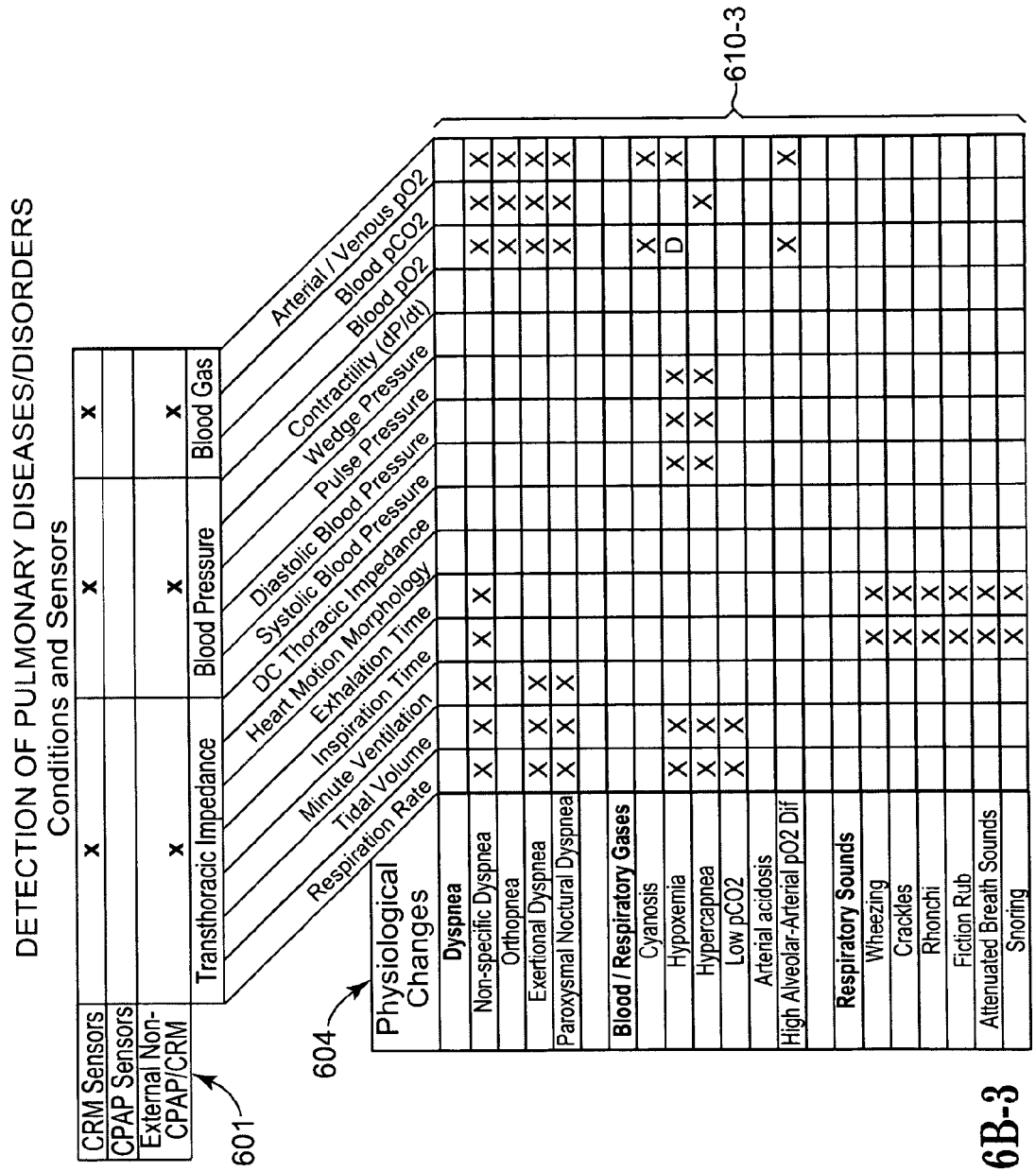
Figures 4, 6B:
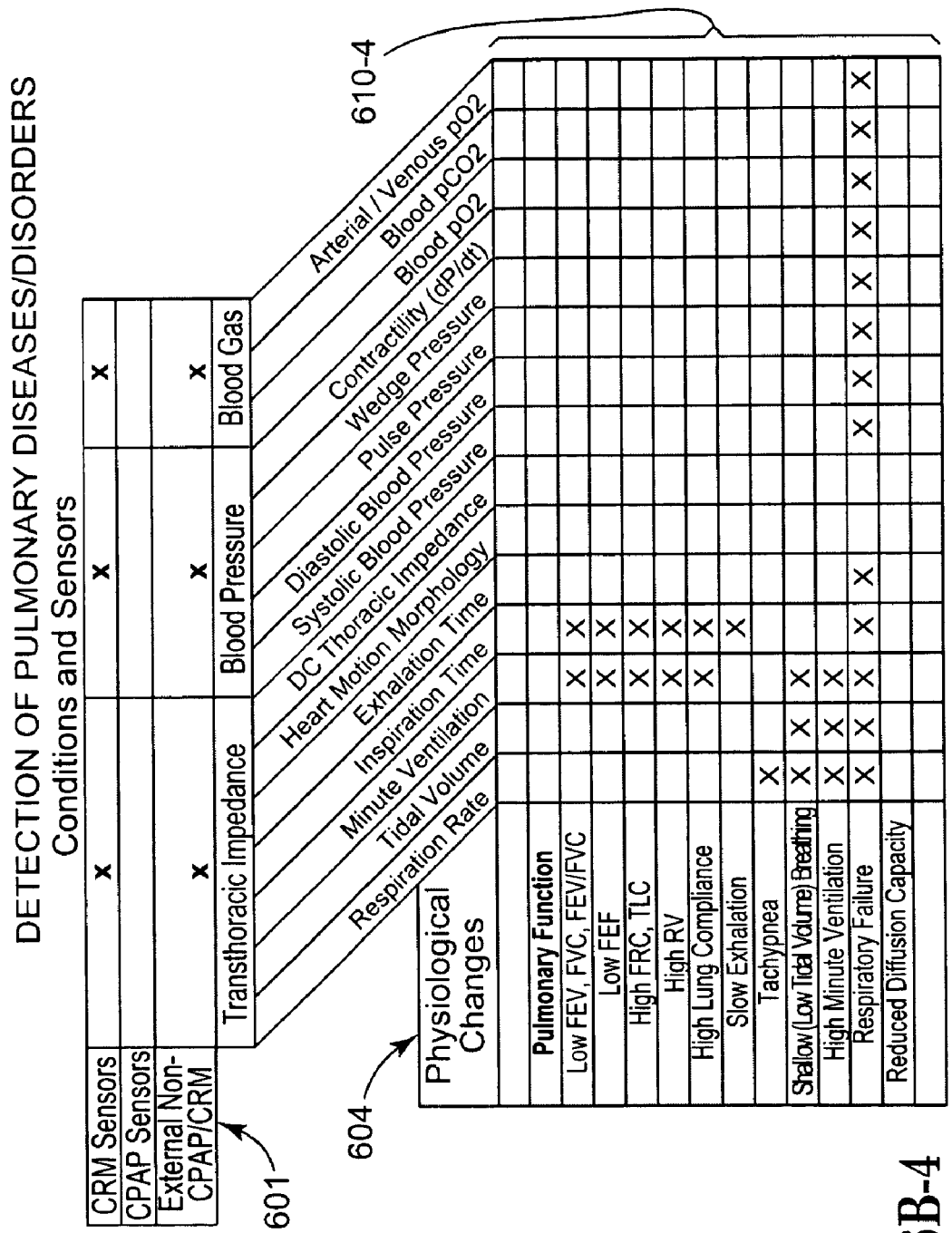
Figures 2, 6C:
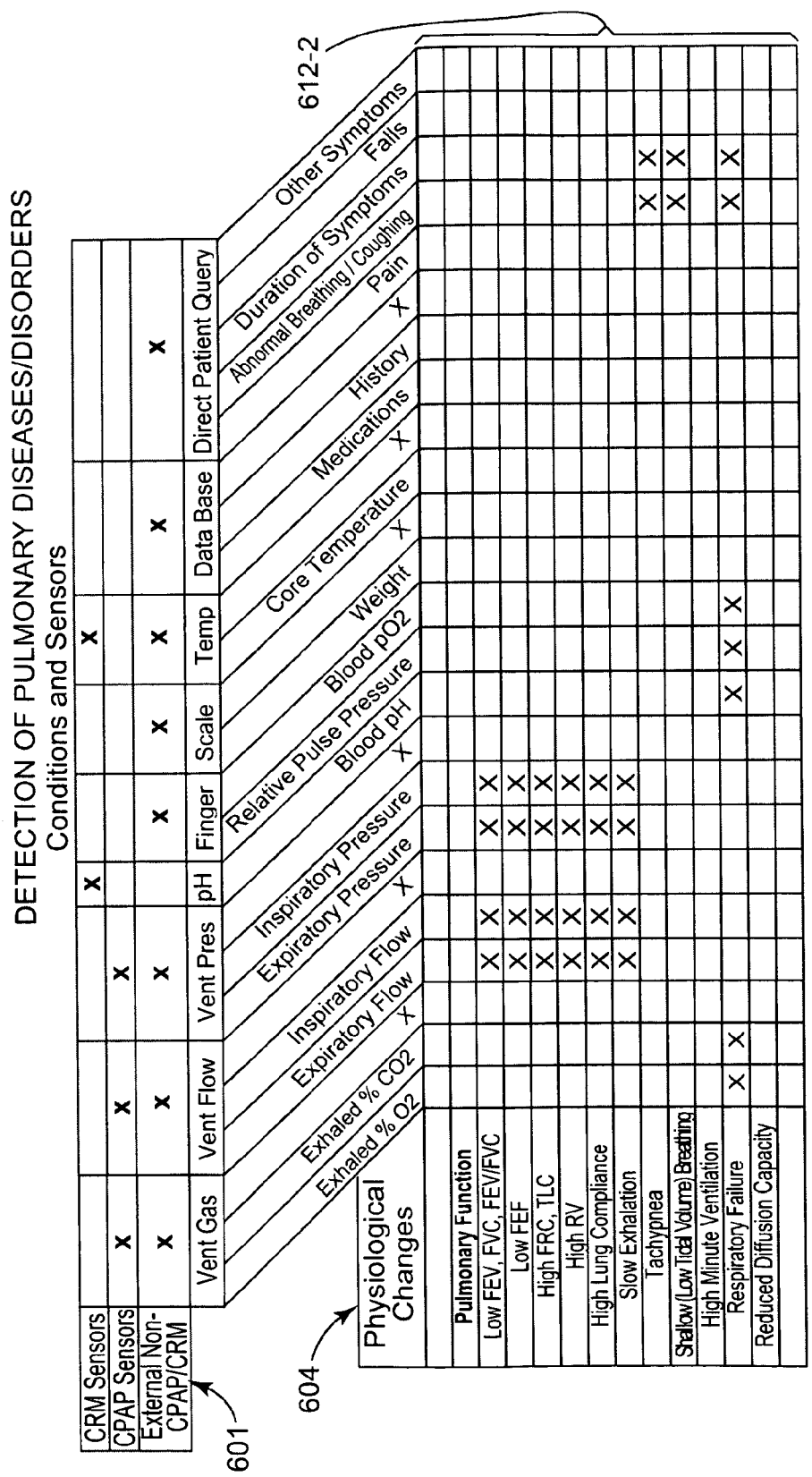
Figures 2, 6D:
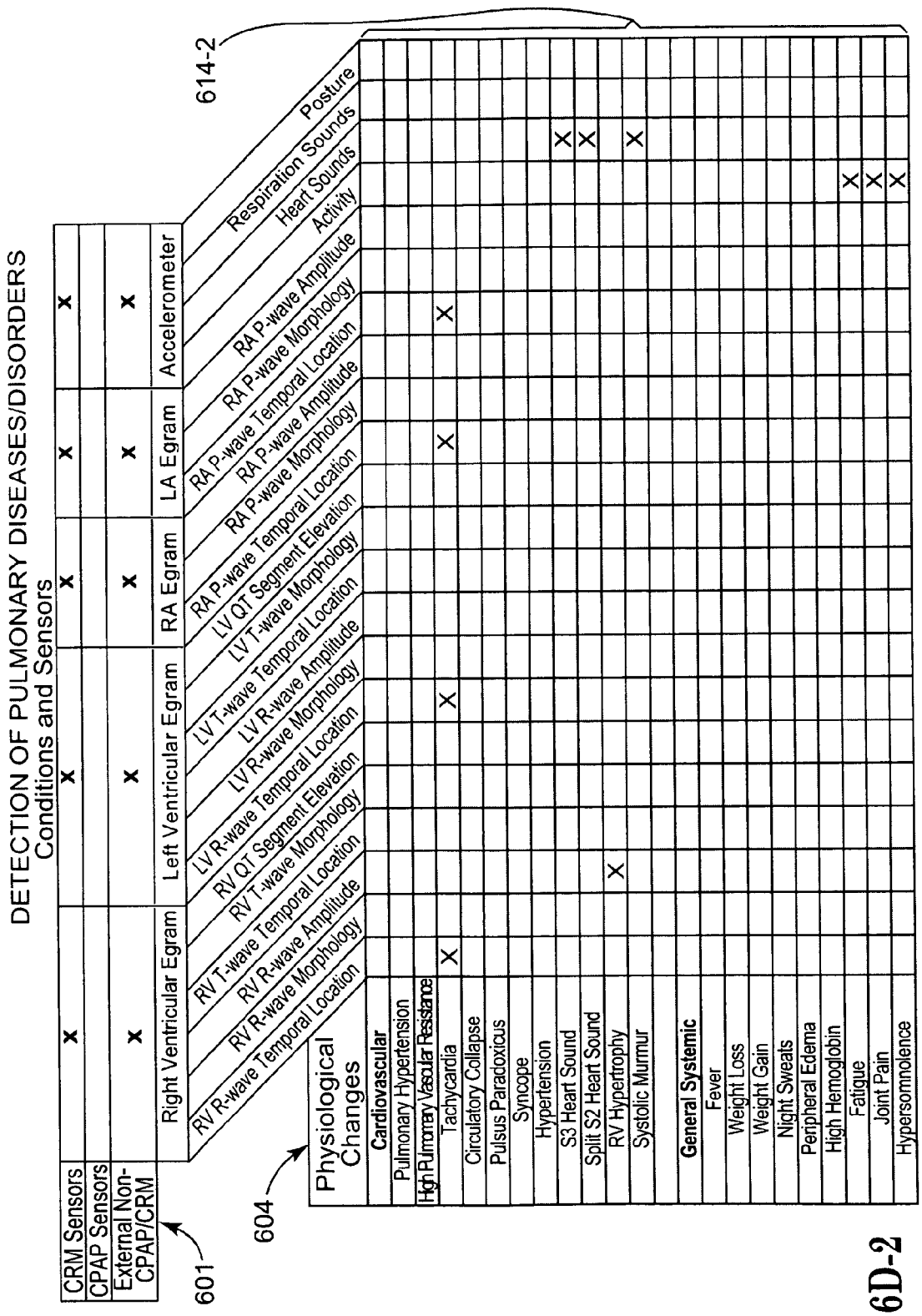
Figures 4, 6D:
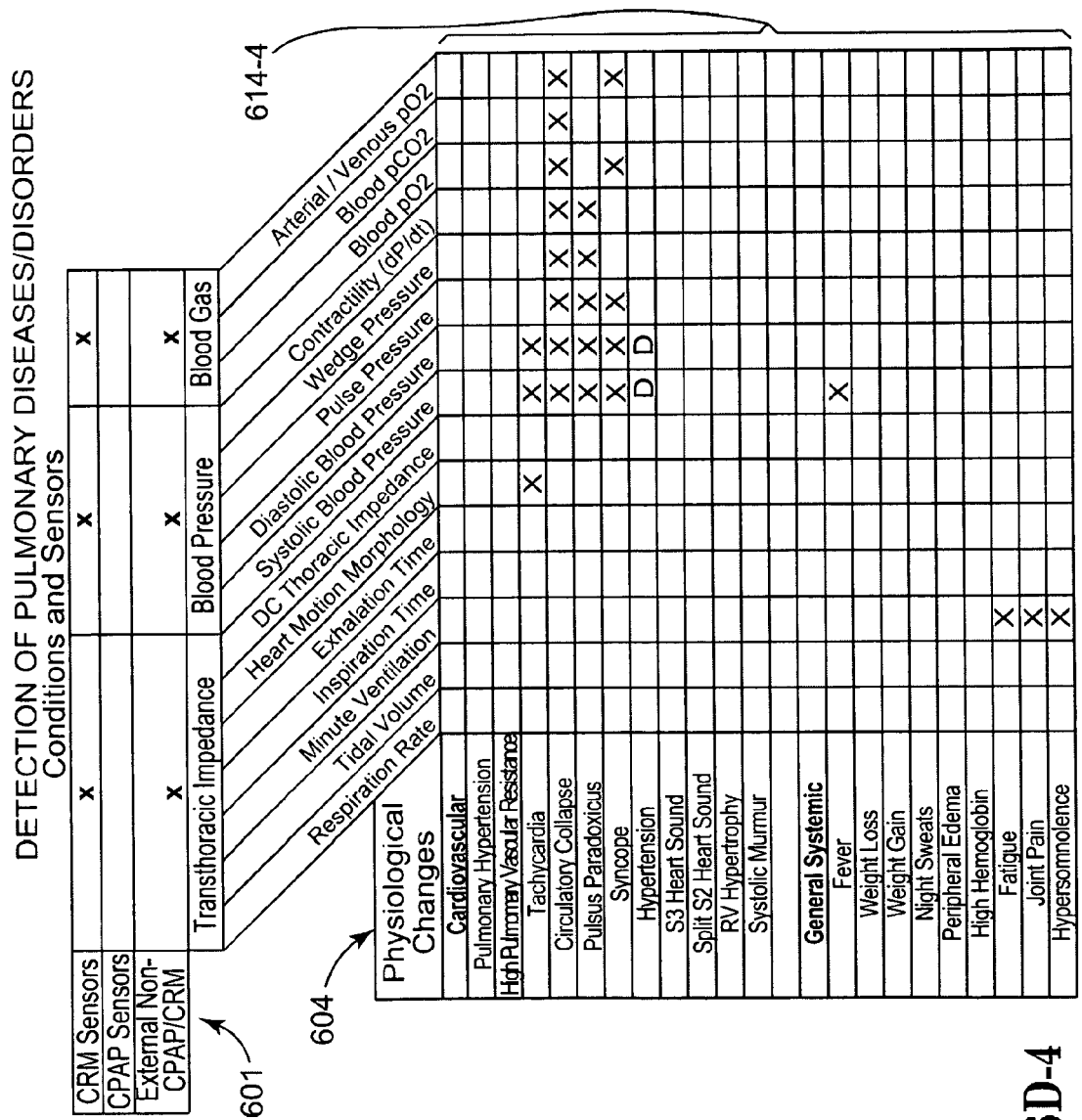
Figures 1, 6E:
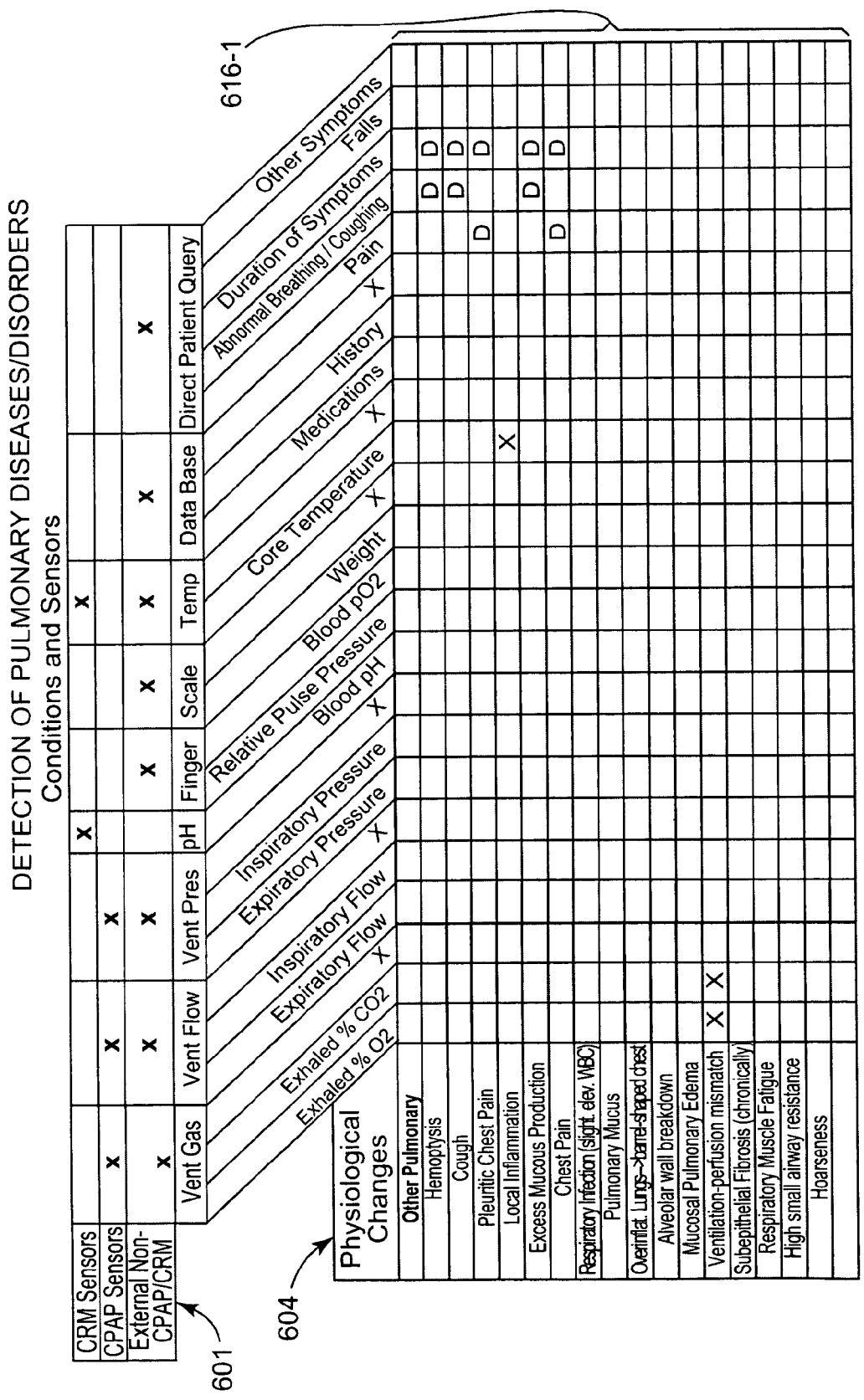
Figures 2, 6E:
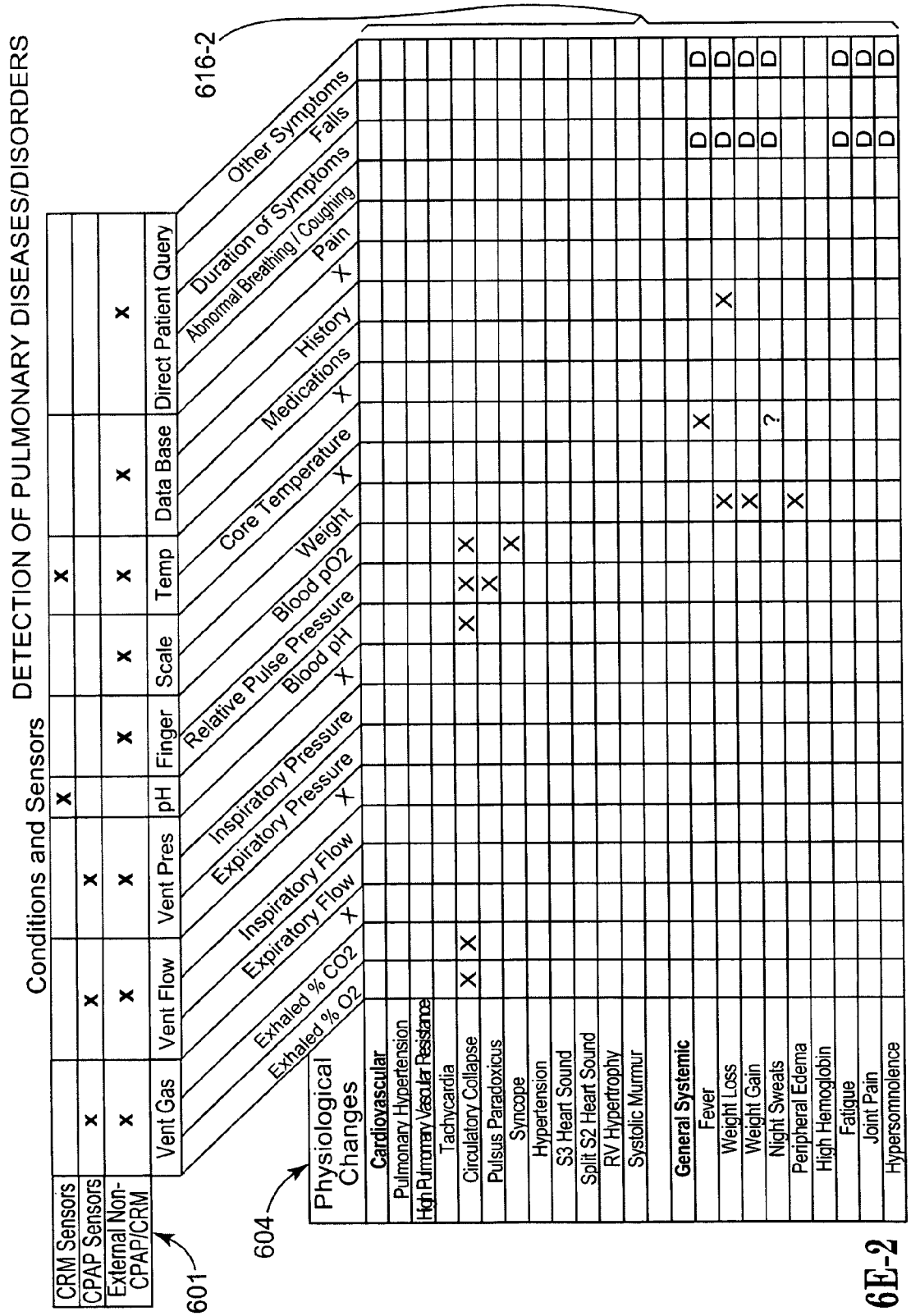

For legibility, the left and right sections 602, 603 of FIG. 6A are divided into sixteen portions, FIGS. 6B-1-6G-2. FIGS. 6B-1-6B-4 represent the upper left portions 610-1 to 610-4 of the left section 602 of FIG. 6A. FIGS. 6C-1-6C-2 represent the upper right portions 612-1 to 612-2 of the left section 602 of FIG. 6A. FIGS. 6D-1-6D-4 represent the lower left portions 614-1 to 614-4 of the left section 602 of FIG. 6A. FIGS. 6E-1-6E-2 represent the lower right portions 616-1 to 616-2 of the left section 602 of FIG. 6A. FIGS. 6F-1-6F-2 represent the upper portions 620-1 to 620-2 of the right section 604 of FIG. 6A. FIGS. 6G-1-6G-2 represent the lower portions 622-1 to 622-2 of the right section 604 of FIG. 6A. Relevant portions of the center section 604 and the top section 601 of FIG. 6A appear in each of the FIGS. 6B-1-6G-2 for convenience.

Figure 6H:
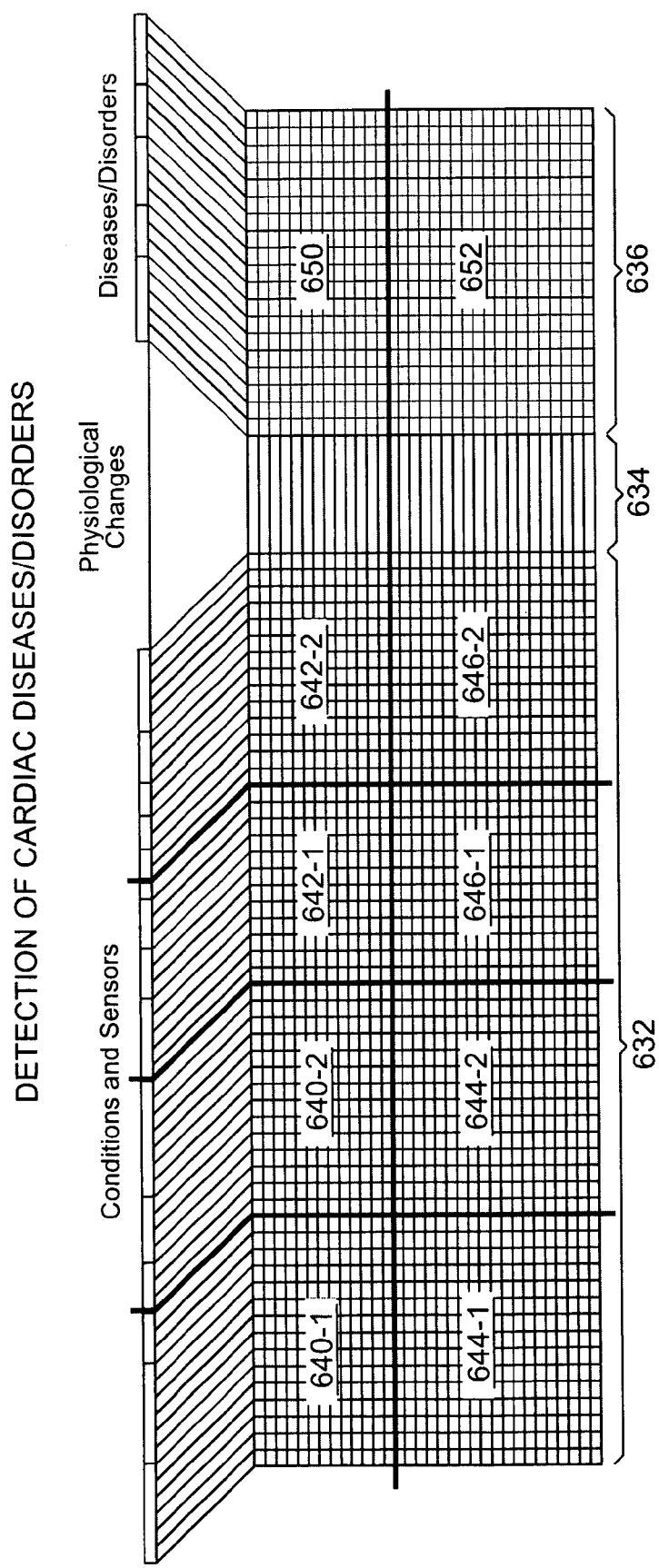

The charts provided in FIGS. 6H-6N illustrate conditions and sensors that may be used to determine physiological changes associated with various cardiac diseases and disorders. The left section 632 of FIG. 6H illustrates various conditions that may be sensed using sensors of a respiratory therapy device (CPAP), a cardiac device (CRM), or an external non-CPAP, non-CRM device. The center section 634 of FIG. 6H provides physiological changes and/or symptoms that may be evaluated using the conditions listed in the left section 632. The right section 636 of FIG. 6H lists cardiac diseases/disorders. The presence of the cardiac diseases/disorders of the right section 636 may be assessed based on the physiological changes and/or symptoms of the center section 634.

Figures 1, 6I:
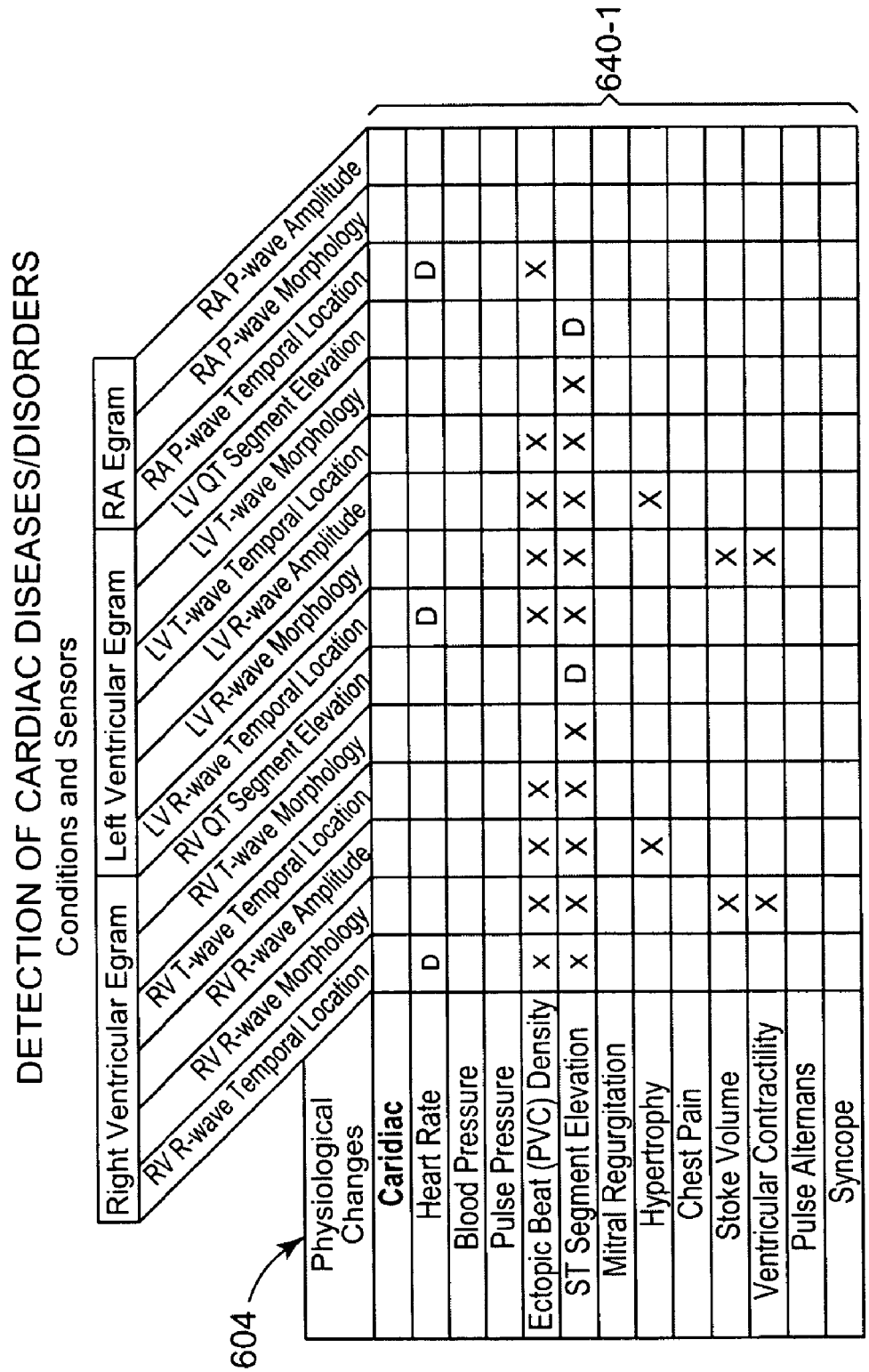
Figures 2, 6I:
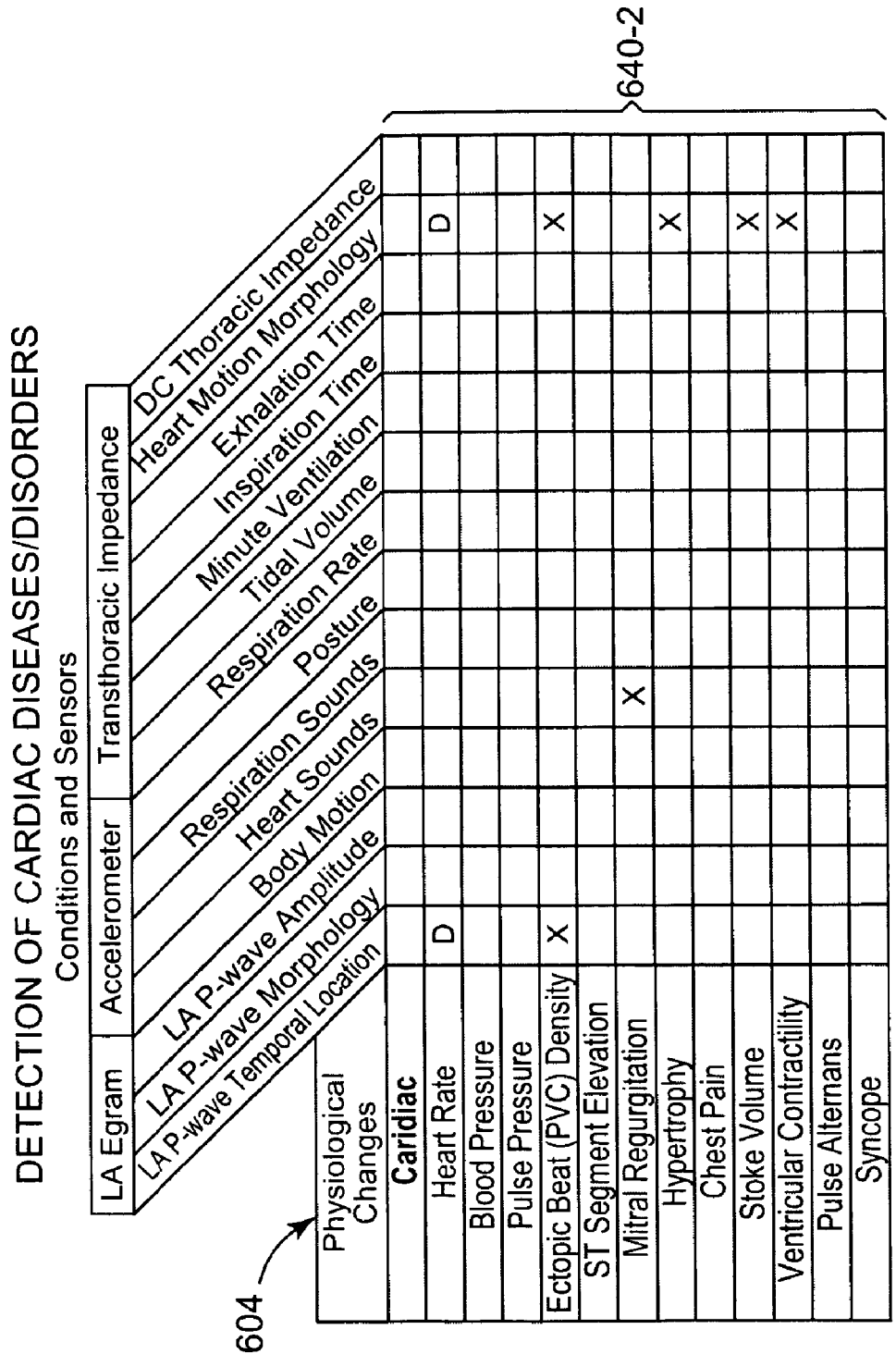
Figures 1, 6J:
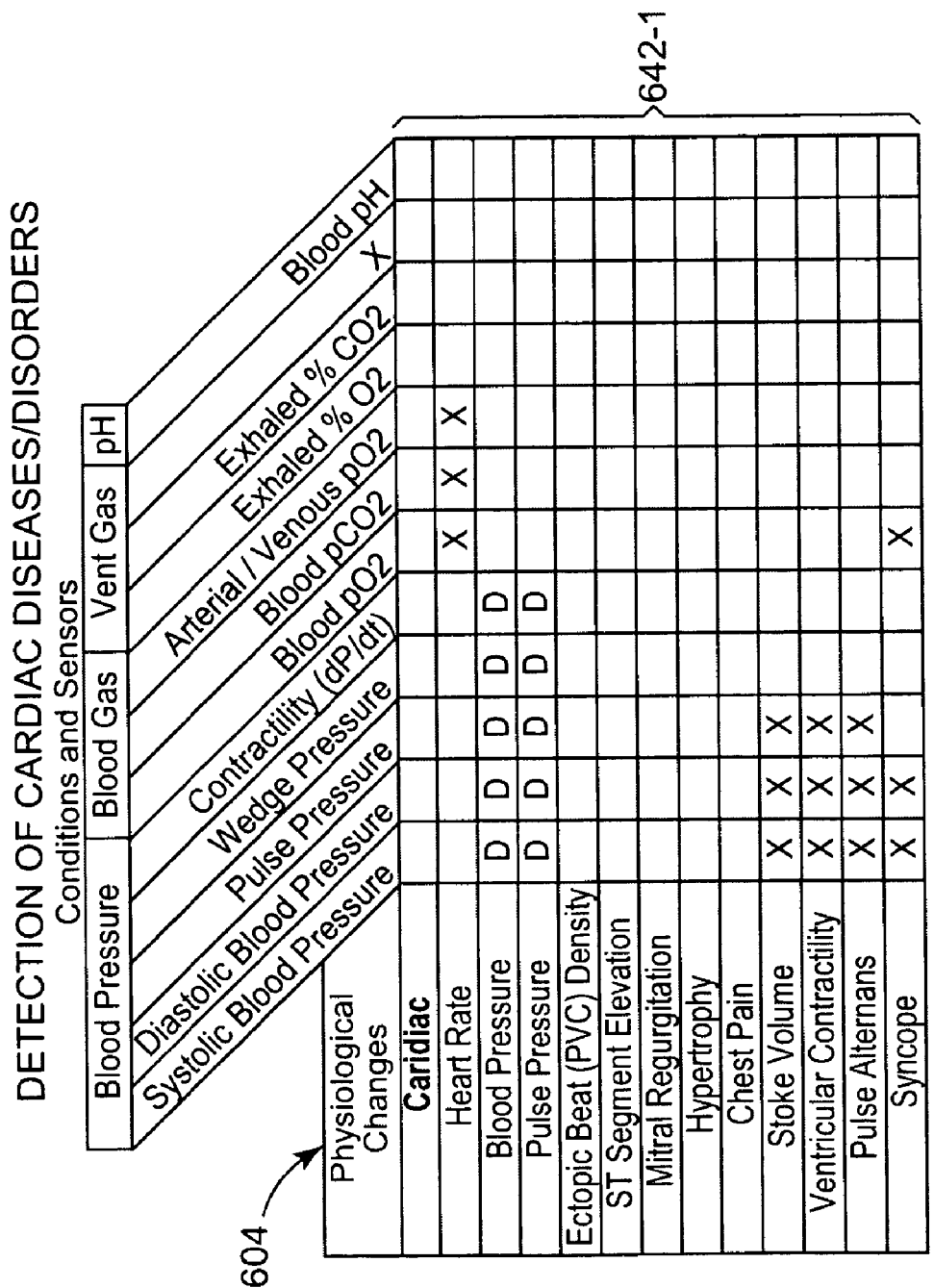
Figures 2, 6J:
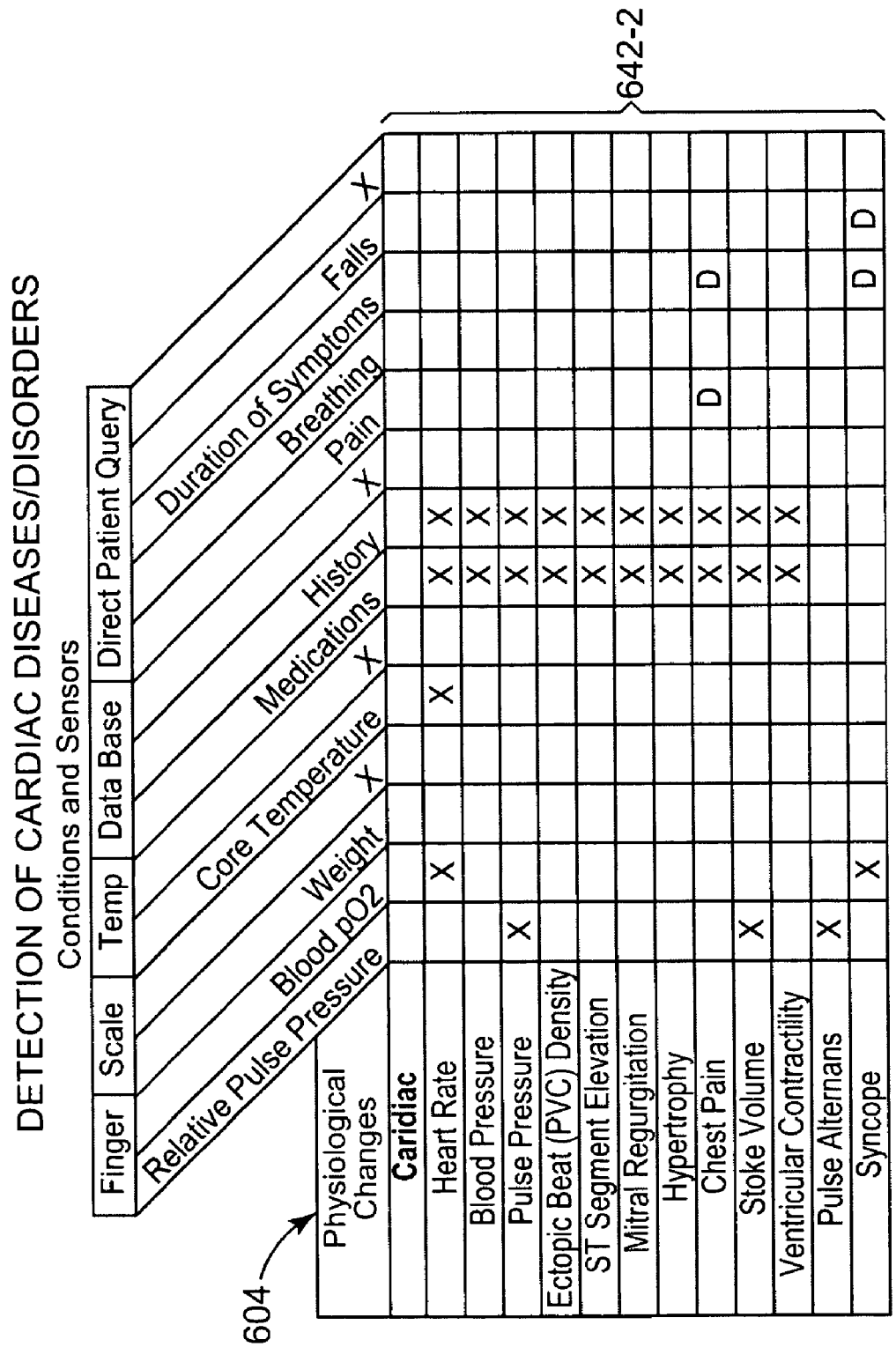
Figures 1, 6K:
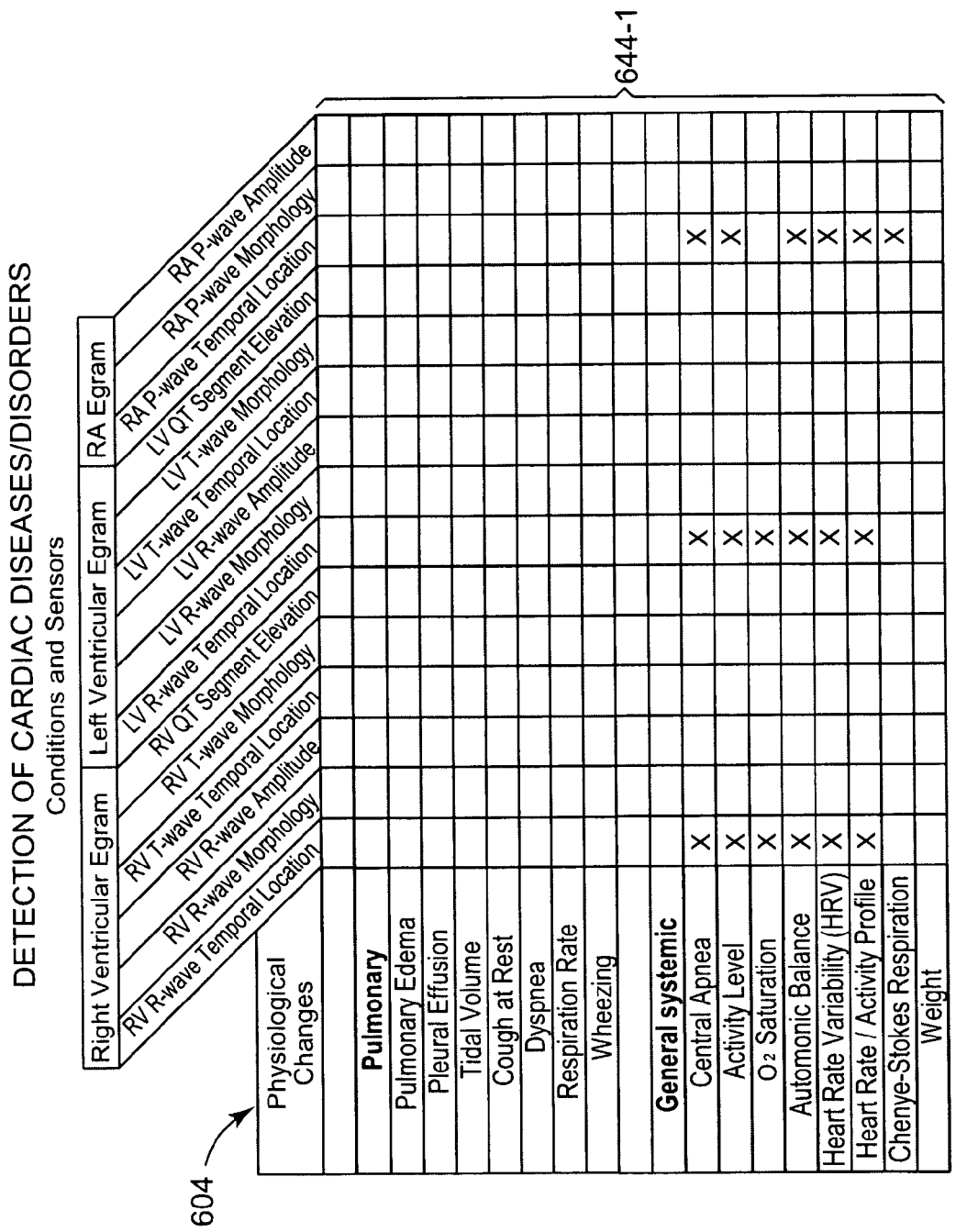
Figures 1, 6L:
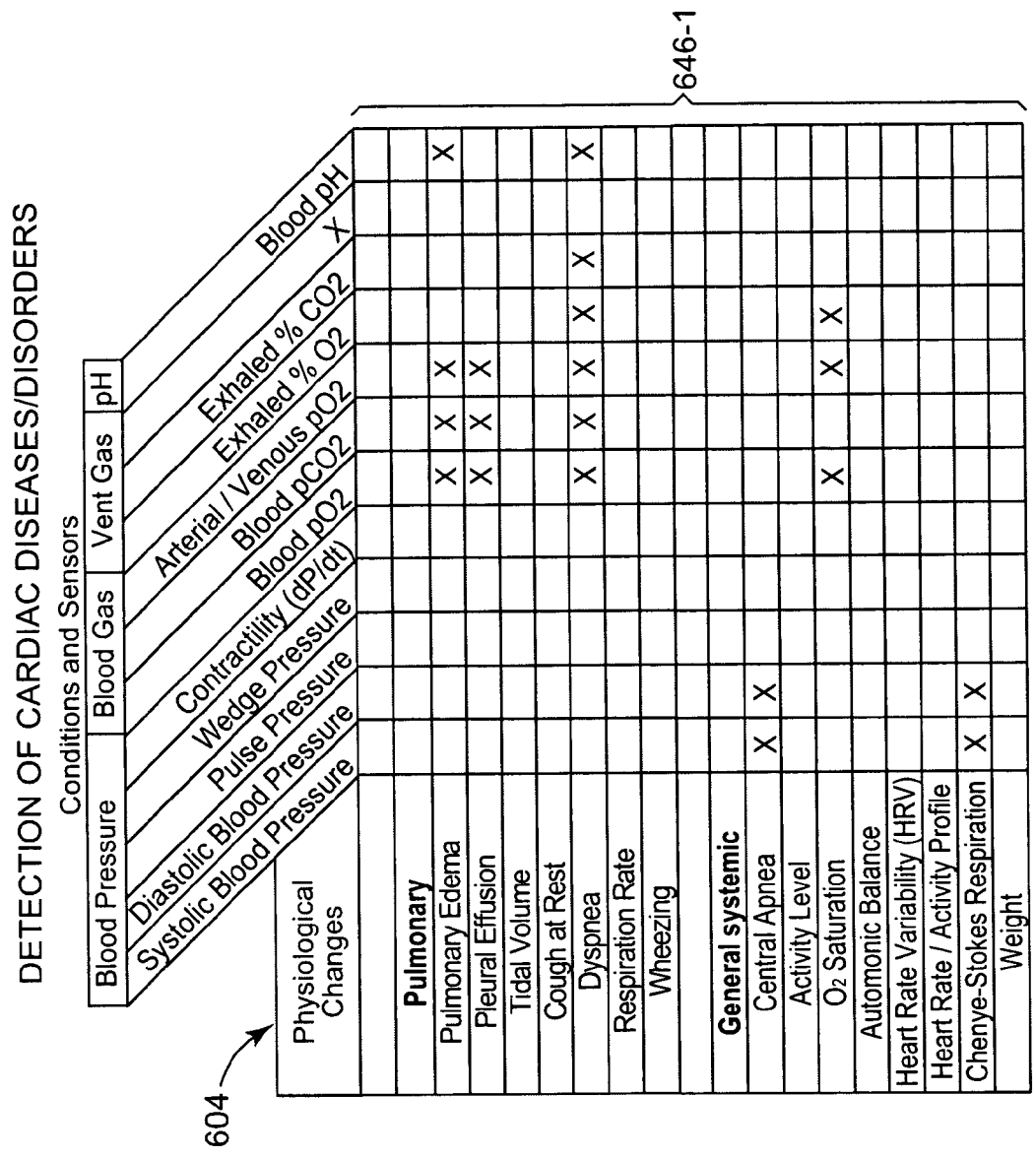
Figures 2, 6L:
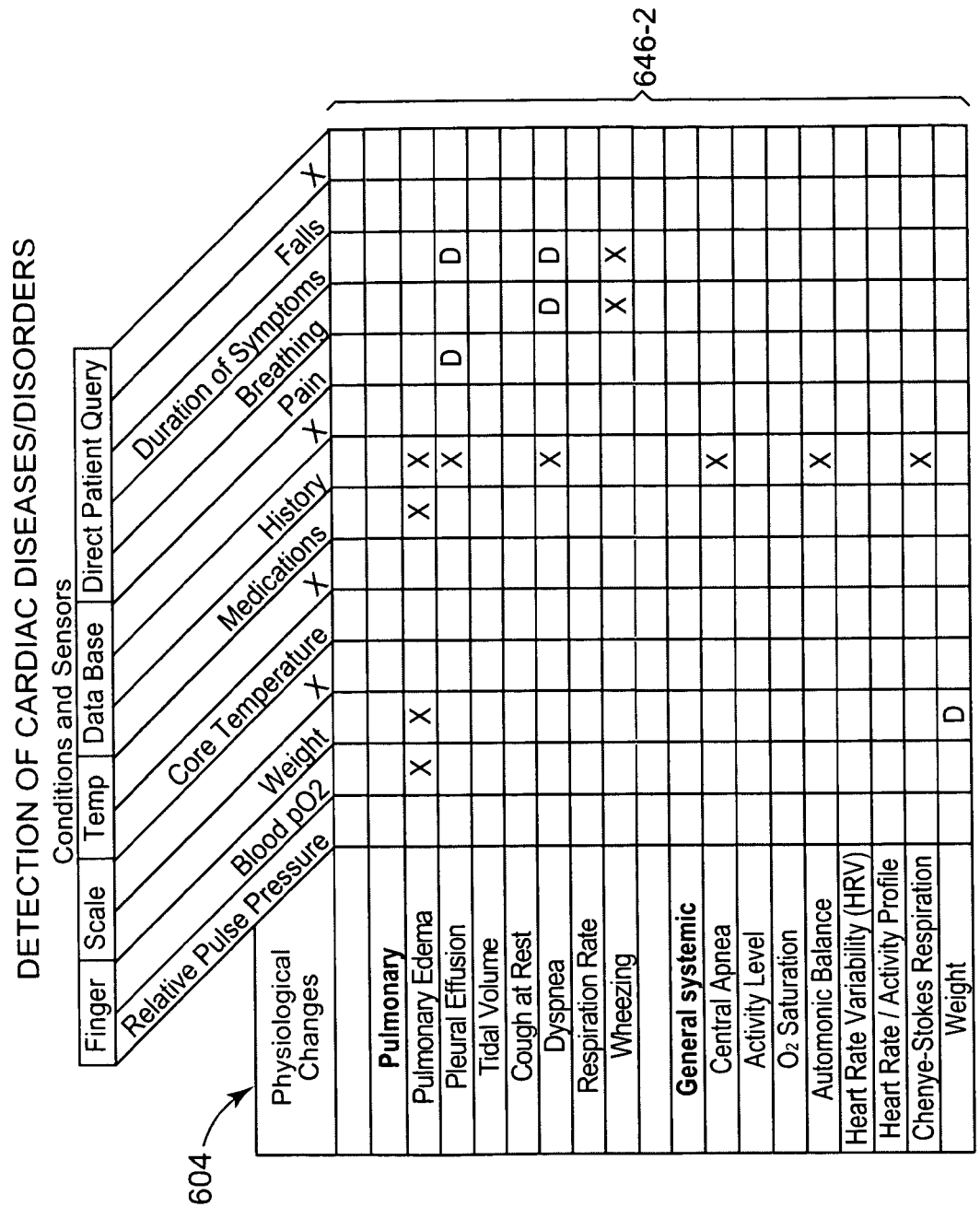

For legibility, the chart of FIG. 6H is divided into ten portions, FIGS. 6I-1-6N. FIGS. 6I-1-6I-2 represent the upper left portion 640 portions 640-1 to 640-2 of the left section 632 of FIG. 6H. FIGS. 6J-1-6J-2 represent the upper right portions 642-1 to 642-2 of the left section 632 of FIG. 6H. FIGS. 6K-1-6K-2 represent the lower left portions 644-1 to 644-2 of the left section 632 of FIG. 6H. FIGS. 6L-1-6L-2 represent the lower right portions 646-1 to 646-2 of the left section 632 of FIG. 6H. FIG. 6M represents the upper portion 650 of the right section 636 of FIG. 6H. FIG. 6N represents the lower portion 652 of the right section 636 of FIG. 6H. Relevant portions of the center section 604 and the top section 601 of FIG. 6H appear in each of the FIGS. 6I-1-6N for convenience.

An example of how FIGS. 6A-6N may be used follows. Referring to FIGS. 6F-1 to 6G-2, the restrictive pulmonary disorder pneumoconiosis produces the physiological changes non-specific dyspnea (FIG. 6 F-1) and cough (FIG. 6G-1). Non-specific dyspnea (FIG. 6 F-1) and cough (FIG. 6G-1) are indicated by X or D marks in the column denoted pneumoconiosis in FIGS. 6F-1 and 6G-2, respectively. An "X" mark indicates that the symptom or physiological change may be derived from the sensed condition. A "D" mark indicates that the symptom or physiological change may be directly determined from the sensed condition. Non-specific dyspnea may be detected based on one or more of the conditions listed in the row for non-specific dyspnea illustrated in FIGS. 6B-1, 6B-3, and 6C-1. The conditions include duration of symptoms, abnormal breathing/coughing, blood pO2, inspiratory flow, expiratory flow, exhaled % CO2 and exhaled % O2, illustrated in FIG. 6C-1. The conditions also include arterial/venous pO2, blood pCO2, blood pO2, exhalation time, inspiration time, minute ventilation, tidal volume, respiration rate, FIG. 6B-3, and/or respiration sounds illustrated in FIG. 6B-1.

The presence of a disorder/disease, such as those listed in FIGS. 6A-6N, may be assessed by based on physiological changes and/or symptoms associated with the disorder/disease. The physiological changes and/or symptoms may be detected using conditions sensed by a sensor system of a respiratory therapy alone or in combination with the sensor systems of other therapeutic or diagnostic medical devices. If the sensed conditions indicate that the physiological changes or symptoms of a disease or disorder are consistent with a threshold level, the presence of the disease or disorder may be determined.

In another example, assessment of disease presence may be based on relative changes in one or more conditions indicative of physiological changes or symptoms caused by the disease. For example, assessment of a presence of a disease or disorder may be accomplished by evaluating the changes in conditions indicative of physiological changes or symptoms caused by the disease. The changes in the one or more conditions may be compared to threshold criteria. If changes in the conditions indicative of physiological changes or symptoms caused by the disease are consistent with threshold levels, a presence of the disease or disorder may be determined.

In a further example, the threshold criteria may involve relationships between the conditions indicative of physiological changes or symptoms caused by the disease. The presence of a disease may be assessed by evaluating relationships between conditions indicative of physiological changes or symptoms caused by the disease. For example, assessment of a disease may involve the determination that levels or amounts of two or more conditions have a certain relationship with one another. If relationships between the conditions indicative of physiological changes or symptoms caused by the disease are consistent with threshold relationship criteria, the disease or disorder may be present.

Techniques for assessing a presence of various pulmonary diseases, aspects of which may be incorporated into the embodiments described herein, are discussed in commonly owned U.S. Pat. No. 7,575,553, incorporated herein by reference.

FIG. 7 is a flowchart illustrating a method in accordance with embodiments of the invention. One or more threshold criteria sets for assessment of cardiopulmonary status based on the disease/disorder presence are established 710. A respiratory therapy device such as a CPAP device may be used to sense 712 conditions modulated by disease symptoms. The sensor information may be collected periodically, e.g., nightly, and stored for evaluation. If a presence of the disease has not been previously determined 715, then the levels of the sensed conditions are compared 720 to a set of criteria associated with the disease. If levels of the conditions are consistent 725 with the threshold criteria levels, then a presence of the disease is determined 730. Therapy may be modified based on the presence of the disease/disorder. In one implementation, therapy may be initiated 735 to treat the disease.

If levels of the conditions are not consistent 725 with the threshold criteria levels, then the system continues to sense conditions modulated by disease symptoms and collect 712 data based on the sensed conditions.

If the presence of the disease was previously determined 715, then the progression of the disease may be monitored 740 based on the conditions and/or criteria used to determine a presence of the disease, or using other conditions and/or criteria. If the disease presence is still detected 745 based on the conditions and criteria used for monitoring, then therapy may be maintained or modified 750 based on the disease progression. Disease progression may be determined, for example, by trending one or more conditions used for monitoring the disease presence over a period of time. Modifications to the therapy may be made based on the condition trends. When the disease presence is no longer detected 745, the therapy may be terminated 755.

A number of the examples presented herein involve block diagrams illustrating functional blocks used for monitoring functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

What is claimed is:

1. A method, comprising:
   sensing a first set of one or more physiological parameters using one or more first sensors of a first medical unit configured to operate outside a patient's body;
   sensing a second set of one or more physiological parameters using one or more second sensors of a second medical unit configured for operation inside the patient's body;
   identifying, based on one or both of the first set of physiological parameters and the second set of physiological parameters, a cardiopulmonary disorder affecting a patient as a breathing rhythm disorder or identifying, based on one or both of the first set of physiological parameters and the second set of physiological parameters, the cardiopulmonary disorder affecting the patient as a non-rhythm breathing disorder, wherein identifying the cardiopulmonary disorder as a non-rhythm breathing disorder comprises discriminating between chronic bronchitis, asthma, emphysema, pulmonary edema and at least one other pulmonary vascular disorder; and
   controlling a therapy delivered to the patient based on the identified cardiopulmonary disorder, wherein at least one of identifying and controlling are performed using circuitry.

2. The method of claim 1, wherein the at least one other pulmonary vascular disorder comprises pulmonary hypertension.

3. The method of claim 1, wherein identifying the non-rhythm breathing disorder comprises identifying an obstructive pulmonary disease or a restrictive pulmonary disease.

4. The method of claim 1, wherein identifying the non-rhythm breathing disorder comprises identifying an infectious pulmonary disease or a non-infectious pulmonary disease.

5. The method of claim 1, wherein identifying the breathing rhythm disorder comprises discriminating between apnea and at least one other breathing rhythm disorder.

6. The method of claim 5, wherein the at least one other breathing rhythm disorder comprises one or more of hypopnea, Cheyne-Stokes respiration, and periodic breathing.

7. The method of claim 1, wherein identifying the cardiopulmonary disorder comprises learning to recognize a presence of the cardiopulmonary disorder based on a history of the physiological parameters.

8. The method of claim 1, wherein identifying the non-rhythm breathing disorder includes identifying a pleural disorder.

9. The method of claim 8, wherein identifying the pleural disorder comprises discriminating between pleural effusion, pneumothorax, and hemothorax.

10. The method of claim 1, wherein controlling the therapy comprises controlling the first medical unit to deliver the therapy.

11. The method of claim 1, wherein controlling the therapy comprises controlling the second medical unit to deliver the therapy.

12. A medical system, comprising:
    one or more first sensors of a first medical unit, the first medical unit configured for operation outside a patient's body, the one or more first sensors configured to sense a first set of one or more physiological parameters;

one or more second sensors of a second medical unit configured for operation inside a patient's body, the one or more second sensors configured to sense a second set of one or more physiological parameters;
a cardiopulmonary status processor configured to
identify, based on one or both of the first set of physiological parameters and the second set of physiological parameters, a cardiopulmonary disorder affecting a patient as a breathing rhythm disorder,
identify, based on one or both of the first set of physiological parameters and the second set of physiological parameters, a cardiopulmonary disorder affecting the patient as a non-rhythm breathing disorder,
wherein the cardiopulmonary status processor is configured to discriminate between chronic bronchitis, asthma, emphysema, pulmonary edema and at least one other pulmonary vascular disorder to identify the non-rhythm breathing disorder; and
a therapy controller configured to control a therapy delivered to the patient based on the identified cardiopulmonary disorder.

13. The medical system of claim 12, wherein the first medical unit comprises an external respiratory therapy device.

14. The medical system of claim 12, wherein the second medical unit comprises an implantable monitoring device.

15. The medical system of claim 12, wherein the second medical unit comprises an implantable therapy device.

16. The medical system of claim 12, wherein the cardiopulmonary status processor is configured to learn to recognize a presence of the cardiopulmonary disorder based on a history of the physiological parameters.

17. The medical system of claim 12, wherein the cardiopulmonary status processor is configured to identify the cardiopulmonary disorder as a pleural disorder.

18. The medical system of claim 17, wherein the cardiopulmonary status processor is configured to discriminate between pleural effusion, pneumothorax, and hemothorax to identify the pleural disorder.

* * * * *